US011278573B2

(12) United States Patent
Centeno

(10) Patent No.: US 11,278,573 B2
(45) Date of Patent: Mar. 22, 2022

(54) METHODS AND COMPOSITIONS TO FACILITATE REPAIR OF AVASCULAR TISSUE

(71) Applicant: Regenerative Sciences, LLC, Broomfield, CO (US)

(72) Inventor: Christopher J. Centeno, Broomfield, CO (US)

(73) Assignee: REGENEXX, LLC, Des Moines, IA (US)

( * ) Notice: Subject to any disclaimer, the term of this patent is extended or adjusted under 35 U.S.C. 154(b) by 0 days.

(21) Appl. No.: 16/441,897

(22) Filed: Jun. 14, 2019

(65) Prior Publication Data

US 2019/0321409 A1 Oct. 24, 2019

Related U.S. Application Data

(63) Continuation of application No. 13/132,840, filed as application No. PCT/US2009/066773 on Dec. 4, 2009, now abandoned.

(60) Provisional application No. 61/154,874, filed on Feb. 24, 2009, provisional application No. 61/120,098, filed on Dec. 5, 2008.

(51) Int. Cl.
| | |
|---|---|
| *A61K 35/28* | (2015.01) |
| *A61K 35/19* | (2015.01) |
| *A61K 38/19* | (2006.01) |
| *A61K 38/18* | (2006.01) |

(52) U.S. Cl.
CPC .............. *A61K 35/28* (2013.01); *A61K 35/19* (2013.01); *A61K 38/18* (2013.01); *A61K 38/19* (2013.01)

(58) Field of Classification Search
None
See application file for complete search history.

(56) References Cited

U.S. PATENT DOCUMENTS

| | | | |
|---|---|---|---|
| 4,832,044 A | 5/1989 | Garg | |
| 5,145,676 A | 9/1992 | Fahey et al. | |
| 5,165,938 A | 11/1992 | Knighton | |
| 5,198,357 A | 3/1993 | Holmovist et al. | |
| 5,226,914 A | 7/1993 | Caplan et al. | |
| 5,486,359 A | 1/1996 | Caplan et al. | |
| 5,693,341 A | 12/1997 | Schroeder et al. | |
| 5,736,396 A | 4/1998 | Bruder et al. | |
| 5,749,874 A | 5/1998 | Schwartz | |
| 5,769,899 A | 6/1998 | Schwartz et al. | |
| 5,770,215 A | 6/1998 | Moshyedi et al. | |
| 5,842,477 A | 12/1998 | Naughton et al. | |
| 6,200,606 B1 | 3/2001 | Peterson et al. | |
| 6,530,956 B1 | 3/2003 | Mansmann | |
| 6,623,733 B1 | 9/2003 | Hossainy et al. | |
| 6,699,471 B2 | 3/2004 | Marco et al. | |
| 6,699,484 B2 | 3/2004 | Whitmore et al. | |
| 6,835,377 B2 | 12/2004 | Goldberg et al. | |
| 6,872,567 B2 | 3/2005 | Thomas et al. | |
| 6,875,605 B1 | 4/2005 | Teng | |
| 7,229,959 B1 | 6/2007 | Drohan et al. | |
| 7,905,863 B1 | 3/2011 | Forrest | |
| 2002/0110544 A1 | 8/2002 | Goldberg et al. | |
| 2003/0050709 A1 | 3/2003 | North et al. | |
| 2003/0203372 A1 | 10/2003 | Ward et al. | |
| 2003/0224411 A1 | 12/2003 | Stanton et al. | |
| 2004/0078077 A1 | 4/2004 | Binette et al. | |
| 2004/0136968 A1 | 7/2004 | Zheng et al. | |
| 2004/0193274 A1 | 9/2004 | Trieu et al. | |
| 2004/0229786 A1 | 11/2004 | Attawia et al. | |
| 2004/0229878 A1 | 11/2004 | DiMauro et al. | |
| 2004/0235166 A1 | 11/2004 | Prockop et al. | |
| 2004/0248293 A1* | 12/2004 | Toner ................... | C12N 5/0604 435/366 |
| 2005/0019865 A1 | 1/2005 | Kihm et al. | |
| 2005/0038520 A1 | 2/2005 | Binette et al. | |
| 2005/0100536 A1 | 5/2005 | Mishra | |
| 2005/0118230 A1 | 6/2005 | Hill et al. | |
| 2005/0205498 A1 | 9/2005 | Sowemimo-Coker et al. | |
| 2005/0265980 A1* | 12/2005 | Chen .................... | C12N 5/0663 424/93.7 |
| 2005/0276792 A1 | 12/2005 | Kaminski et al. | |
| 2006/0073124 A1 | 4/2006 | Garcia Castro et al. | |
| 2006/0128016 A1 | 6/2006 | Tokushima et al. | |
| 2006/0275273 A1 | 12/2006 | Seyedin et al. | |
| 2007/0087032 A1 | 4/2007 | Chang et al. | |
| 2007/0122904 A1 | 5/2007 | Nordon | |
| 2007/0128722 A1 | 6/2007 | Lin et al. | |
| 2007/0213822 A1 | 9/2007 | Trieu et al. | |

(Continued)

FOREIGN PATENT DOCUMENTS

| | | |
|---|---|---|
| EP | 2257176 | 9/2013 |
| KR | 2003 024028 | 3/2003 |

(Continued)

OTHER PUBLICATIONS

DiGirolamo et al., "Propagation and senescence of human marrow stromal cells in culture: a simple colony-forming assay identifies samples with the greatest potential to propagate and differentiate", British Journal of Haematology, 1999, vol. 107, pp. 275-281. (Year: 1999).*

Ginouves et al., "PHDs overactivation during chronic hypoxia "desensitizes" HIF and protects cells from necrosis", PNAS, Mar. 25, 2008, vol. 105, No. 12, pp. 4745-4750. (Year: 2008).*

Elabd et al. "Intra-discal injection of autologous, hypoxic cultured bone marrow-derived mesenchymal stem cells in five patients with chronic lower back pain: a long-term safety and feasibility study", Journal of Translational Medicine, Aug. 31, 2016, 14:253, pp. 1-9. (Year: 2016).*

(Continued)

*Primary Examiner* — Laura Schuberg
(74) *Attorney, Agent, or Firm* — K&L Gates LLP

(57) ABSTRACT

Compositions and methods are provided for repairing damaged avascular zones, including intervertebral disc, in a patient in need thereof.

13 Claims, 14 Drawing Sheets

(56) References Cited

U.S. PATENT DOCUMENTS

| | | | |
|---|---|---|---|
| 2008/0038233 | A1 | 2/2008 | Freemont et al. |
| 2009/0010896 | A1 | 1/2009 | Centeno et al. |
| 2009/0208464 | A1 | 8/2009 | Centeno |
| 2009/0274665 | A1 | 11/2009 | Akabutu et al. |
| 2010/0168022 | A1 | 7/2010 | Centeno |
| 2011/0052533 | A1 | 3/2011 | Centeno |
| 2011/0054929 | A1 | 3/2011 | Centeno |
| 2011/0200642 | A1 | 8/2011 | Centeno |
| 2011/0276001 | A1 | 11/2011 | Centeno |
| 2013/0084341 | A1 | 4/2013 | Centeno |
| 2013/0108593 | A1 | 5/2013 | Centeno |

FOREIGN PATENT DOCUMENTS

| | | |
|---|---|---|
| WO | WO 1997/034614 | 9/1997 |
| WO | WO 1998/51317 | 11/1998 |
| WO | WO 2001/080865 | 11/2001 |
| WO | WO 2004/067704 | 8/2004 |
| WO | WO 2005/046761 | 5/2005 |
| WO | WO 2005/085421 | 9/2005 |
| WO | WO 2007/087519 | 8/2007 |
| WO | WO 2007/136673 | 11/2007 |
| WO | WO 2008/034803 | 3/2008 |
| WO | WO 2009/006161 | 1/2009 |
| WO | WO 2009/085969 | 7/2009 |
| WO | WO 2009/114785 | 9/2009 |
| WO | WO 2010/065854 | 6/2010 |

OTHER PUBLICATIONS

Ando et al. (2007) "Cartilage repair using an in vitro generated scaffold-free tissue-engineered construct derived from porcine synovial mesenchymal stem cells" Biomaterials 1-9. Available Website: www.sciencedirect.com.
Castro et al. (2002) "Failure of Bone Marrow Cells to Transdifferentiate into Neutral Cells In Vivo" Science 297:1299.
Centeno et al. (2008) "Regeneration of meniscus cartilage in a knee treated with percutaneously implanted autologous mesenchymal stem cells" Medical Hypotheses 71:900-908.
Centeno and Faulkner (2012) "The Use of Mesenchymal Stem Cells in Orthopedics" Stem Cells and Cancer Stem Cells 1:173-179.
Koga et al. (2008) "Local adherent technique for transplanting mesenchymal stem cells as a potential treatment of cartilage defect" Arthritis Research & Therapy 10(R84), 1-10. Available web site: http://arthritis-research.com/content/10/4/R84 (Adherent Technique).
Koga et al. (2008) "Local adherent technique for transplanting mesenchymal stem cells as a potential treatment of cartilage defect" Arthritis Research & Therapy 10(R84), 1-10. Available web site: http://arthritis-research.com/content/10/4/R84 (Novel Technique).
Mezey et al and Castro et al (2003) "Comment on and Response to Comment on Failure of Bone Marrow Cells to Transdifferentiate into Neutral Cells In Vivo" Science 299:1184b-1184c.
Risbud et al., "Differentiation of Mesenchymal Stem Cells Towards a Nucleus Pulposus-like Phenotype In vitro: Implications for Cell-Based Transplantation Therapy", SPINE, 2004, vol. 29, No. 23, pp. 2627-2632.
Steck et al., "Induction of Intervertebral Disc-Like Cells From Adult Mesenchymal Stem Cells", Stem Cells, 2005, vol. 23, pp. 403-411.
Tosh et al (2002) "Conversion of Pancreatic Cells to Hepatocytes" Biochem. Soc. Trans. 30:51-55.
Avascular Necrosis in patient education of Illinois Bone and Joint Institute. 2003 downloaded from the hipdoc.com/avas.htm. p. 1-2.
Hip Replacement Surgery. John Hopkins Medicine. Downloaded on Jul. 14, 2012 from www.hopkinsmedicine.org/healthlibrary/conditions/adult/orthopaedic_disorders/hip_replacement_surger_85, P01372. p. 1-4.
Kravitz et al. "How Do Muscles Grow", IDEA Fitness Journal; 3(2), 23-25 (2006) (http://www.unm.edu/kravitz/Article%20folder/musclesgrowLK.html).
Regenexx™ PR article published Nov. 8, 2007; downloaded May 14, 2012.
Acosta et al. (2005) "The Potential Role of Mesenchymal Stem Cell Therapy for Intervertebral Disc Degeneration: A Critical Overview" Neurosurg. Focus 19(3):E4.
Ahuja et al. (1995) "Identification of Two Subpopulations of Rat Monocytes Expressing Disparate Molecular Forms and Quantities of CD43" Cell Immunol. 163(1):59-69.
Alhadlaq and Mao (2004) "Mesenchymal Stem Cells: Isolation and Therapeutics" Stem Cells Dev. 13(4):436-448.
Anitua et al. (2004) "Autologous Platelets as a Source of Proteins for Healing and Tissue Regeneration" Thromb. Haemost. 91:4-15.
Baecher-Allan et al. (2005) "Functional Analysis of Highly Defined, FACS-Isolated Populations of Human Regulatory CD4+CD25+T Cells" Clinical Immunology 115:10-18.
Barry (2003) "Mesenchymal Stem Cell Therapy in Joint Disease" Novartis Found. Symp. 249:86-102, 170-4, 239-41.
Bensaïd et al. (2003) "A Biodegradable Fibrin Scaffold for Mesenchymal Stem Cell Transplantation" Biomaterials 24:2497-2502.
Bernardo et al. (2007) "Optimization of In Vitro Expansion of Human Multipotent Mesenchymal Stromal Cells for Cell-Therapy Approaches: Further Insights in the Search for a Fetal Calf Serum Substitute" J. Cell. Physiol. 211:121-130.
Billard et al. (2000) "Switch in the Protein Tyrosine Phosphatase Associated with Human CD100 Semaphorin at Terminal B-Cell Differentiation Stage" Blood 95(3):965-972.
Bircher et al. (1988) "Discitis Following Lumbar Surgery" Spine 13(1):98-102.
Borner and Follath (1989) "Antibiotic Therapy and Long-Term Outcome in Patients with Vertebral Osteomyelitis" Schweiz Med. Wochenschr. 119(1):19-21 (German, English Abstract Only).
Brisby et al. (2004) "Cell Therapy for Disc Degeneration-Potentials and Pitfalls" Orthop. Clin. North Am. 35(1):85-93.
Buckwalter and Mankin (1998) "Articular Cartilage: Degeneration and Osteoarthritis, Repair, Regeneration, and Transplantation" AAOS Instr. Course Leet. 47:487-504.
Bühring et al (1999) "The Monoclonal Antibody 97A6 Defines a Novel Surface Antigen Expressed on Human Basophils and Their Multipotent and Unipotent Progenitors" Blood 94(7):2343-2356.
Caligiuri et al (1990) "Functional Consequences of Interleukin 2 Receptor Expression on Resting Human Lymphocytes. Identification of a Novel Natural Killer Cell Subset with High Affinity Receptors" J. Exp. Med. 171:1509-1526.
Caplan and Bruder (2001) "Mesenchymal Stem Cells: Building Blocks for Molecular Medicine in the 21st Century" Trends Mol. Med. 7(6):259-264.
Caplan (1991) "Mesenchymal Stem Cells" J. Orthop. Res. 9(5):641-650.
Cashman et al (1990) "Mechanisms that Regulate the Cell Cycle Status of Very Primitive Hematopoietic Cells in Long-Term Human Marrow Cultures. I. Stimulatory Role of a Variety of Mesenchymal Cell Activators and Inhibitory Role of TGF-Beta" Blood 75(1):96-101.
Cassiede et al (1996) "Osteochondrogenic Potential of Marrow Mesenchymal Progenitor Cells Exposed to TGF-β1 or PDGF-BB as Assayed In Vivo and In Vitro" J. of Bone and Miner. Res. 11(9):1264-1273.
Centeno et al (2006) "Partial Regeneration of the Human Hip Nucleated Cell Transfer: A Case Study" Pain Physician 9:253-256.
Charalambous et al (2003) "Septic Arthritis Following Intra-Articular Steroid Injection of the Knee-a Survey of Current Practice Regarding Antiseptic Technique used During Intra-Articular Steroid Injection of the Knee" Clin. Rheumatol. 22:386-390.
Chazerain et al (1999) "Septic Hip Arthritis After Multiple Injections into the Joint of Hyaluronate and Glucocorticoid" Rev. Rhum. Engl. Ed. 66(7-9):436-437.
Crisostomo et al (2006) "High Passage Number of Stem Cells Adversely Affects Stem Cell Activation and Myocardial Protection" Shock 26(6):575-580.
D'lppolito et al (1999) "Age-Related Osteogenic Potential of Mesenchymal Stromal Stem Cells from Human Verterbral Bone Marrow" J. Bone Miner. Res. 14(7):1115-122.

(56) References Cited

OTHER PUBLICATIONS

Dall et al (1987) "Postoperative Discitis. Diagnosis and Management" Clin. Orthop. Relat. Res. 224:138-146.
Deschaseaux et al (2003) "Direct Selection of Human Bone Marrow Mesenchymal Stem Cells Using an Anti-CD49a Antibody Reveals Their CD45$^{med,low}$ Phenotype" British Journal of Haematology 122:506-517.
Doucet et al (2005) "Platelet Lysates Promote Mesenchymal Stem Cell Expansion: A Safety Substitute for Animal Serum in Cell-Based Therapy Applications" J. Cell. Physiol. 205:228-236.
Elghetany and Patel (2002) "Assessment of CD24 Expression on Bone Marrow Neutrophilic Granulocytes: CD24 is a Marker for the Myelocytic Stage of Development" Am. J. Hematol. 71:348-349.
Fang et al (2004) "Biocompatibility Studies on Fibrin Glue Cultured with Bone Marrow Mesenchymal Stem Cells In Vitro" J. of Huazhong. Univ. of Sci. Technolog. Med. Sci. 24(3):272-274.
Fiedler et al (2002) "BMP-2, BMP-4, and PDGF-bb Stimulate Chemotactic Migration of Primary Human Mesenchymal Progenitor Cells" J. Cell. Biochem. 87:305-312.
Fiedler et al (2004) "To Go or Not to Go: Migration of Human Mesenchymal Progenitor Cells Stimulated by Isoforms of PDGF" J. Cell. Biochem. 93:990-998.
Fortier et al (1998) "Isolation and Chondrocytic Differentiation of Equine Bone Marrow-Derived Mesenchymal Stem Cells" Am. J. Vet. Res. 59(9):1182-1187.
Fraser et al (1993) "Each Hypersensitive Site of the Human Beta-Globin Locus Control Region Confers a Different Developmental Pattern of Expression on the Globin Genes" Genes & Development 7:106-113.
Fujiwara et al (1994) "Acute Purulent Discitis with Epidural Abscess of the Cervical Spine in an Adult" Neurol. Med. Chir. (Tokyo) 34(6):382-384.
Gazzit et al (1995) "Purified CD34$^+$ Lin$^-$ Thy$^+$ Stem Cells do Not Contain Clonal Myeloma Cells" Blood 86(1):381-389.
Gibson and Waddell (2005) "Surgery for Degenerative Lumbar Spondylosis: Updated Cochrane Review" Spine 30(20):2312-2320.
Gruber and Hanley (2003) "Recent Advances in Disc Cell Biology" Spine 28(2):186-193.
Gruber et al (2004) "Platelet-Released Supernatants Increase Migration and Proliferation, and Decrease Osteogenic Differentiation of Bone Marrow-Derived Mesenchymal Progenitor Cells Under In Vitro Conditions" Platelets 15(1):29-35.
Gustafson et al (1989) "Further Investigations into the Potentiation of Infection by Intra-Articular Injection of Polysulfated Glycosaminoglycan and the Effect of Filtration and Intra-Articular Injection of Amikacin" Am. J. Vet. Res. 50(12):2018-2022.
Hickstein et al (1992) "Identification of the Promoter of the Myelomonocytic Leukocyte Integrin CD11b" Proc. Natl. Acad. Sci. USA 89(6):2105-2109.
Hirschi et al (1999) "Endothelial Cells Modulate the Proliferation of Mural Cell Precursors Via Platelet-Derived Growth Factor-BB and Heterotypic Cell Contact" Circ. Res. 84(3):298-305.
Hoelscher et al (2000) "Effects of Very High Antibiotic Concentrations on Human Intervertebral Disc Cell Proliferation, Viability, and Metabolism In Vitro" Spine 25(15):1871-1877.
Huang and Terstappen (1994) "Formation of Haematopoietic Microenvironment and Haematopoietic Stem Cells from Single Human Bone Marrow Stem Cells" Nature 368(6472):664.
Huss (2000) "Perspectives on the Morphology and Biology of CD34-Negative Stem Cells" J. Hematother. Stem Cell Res. 9:783-793.
Iversen et al (1992) "Prognosis in Postoperative Discitis, A Retrospective Study of 111 Cases" Acta Orthop. Scand. 63(3):305-309.
Johnstone and Yoo (1999) "Autologous Mesenchymal Progenitor Cells in Articular Cartilage Repair" Clin. Orthop. Relat. Res. 367 Suppl:S156-162.
Kambin and Schaffer (1989) "Percutaneous Lumbar Discectomy Review of 100 Patients and Current Practice" Clin. Orthop. Relat. Res. 238:24-34.
Kang et al (2005) "Role of c-Jun N-Terminal Kinase in the PDGF-Induced Proliferation and Migration of Human Adipose Tissue-Derived Mesenchymal Stem Cells" J. Cell. Biochem. 95:1135-1145.
Kaps et al (2002) "Human Platelet Supernatant Promotes Proliferation but Not Differentiation of Articular Chondrocytes" Med. Biol. Eng. Comput. 40(4):485-490.
Katz et al (1987) "Effect of Platelet-Derived Growth Factor on Enriched Populations of Haemopoietic Progenitors from Patients with Chronic Myeloid Leukaemia" Leuk. Res. 11(4):339-344.
Kilian et al (2004) "Effects of Platelet Growth Factors on Human Mesenchymal Stem Cells and Human Endothelial Cells In Vitro" Eur. J. Med. Res. 9(7):337-344.
Kirshenbaum et al (1999) "Demonstration that Human Mast Cells Arise from a Progenitor Cell Population that is CD34+, c-kit+, and Expresses Aminopeptidase N (CD13)" Blood 94:2333-2342.
Kitoh et al (2004) "Transplantation of Marrow-Derived Mesenchymal Stem Cells and Platelet-Rich Plasma During Distraction Osteogenesis—a Preliminary Result of Three Cases" Bone 35:892-898.
Koh et al (2005) "Co-Culture of Human CD34+ Cells with Mesenchymal Stem Cells Increases the Survival of CD34+ Cells Against the 5-Aza-Deoxycytidine- or Trichostatin A-Induced Cell Death" Biochem. Biophys. Res. Commun. 329:1039-1045.
Kortelainen and Särkioja (1990) "Fatal Complications of Intramuscular and Intra-Articular Injections" Z Rechtsmed. 103:547-554.
Laiho and Kotilainen (2001) "Septic Arthritis Due to Prevotella Bivia After Intra-Articular Hip Joint Injection" Joint Bone Spine 68:443-444.
Lange et al (2007) "Accelerated and Safe Expansion of Human Mesenchymal Stromal Cells in Animal Serum-Free Medium for Transplantation and Regenerative Medicine" Journal of Cellular Physiology 213(1):18-26.
Luyten (2004) "Mesenchymal Stem Cells in Osteoarthritis" Curr. Opin. Rheumatol. 16:599-603.
Magne et al (2005) "Mesenchymal Stem Cell Therapy to Rebuild Cartilage" Trends Mol. Med. 11(11):519-526.
Martineau et al (2004) "Effects of Calcium and Thrombin on Growth Factor Release from Platelet Concentrates: Kinetics and Regulation of Endothelial Cell Proliferation" Biomaterials 25:4489-4502.
Medina et al (2000) "Purification of Human Tonsil Plasma Cells: Pre-Enrichment Step by Immunomagnetic Selection of CD31$^+$ Cells" Cytometry 39(3):231-234.
Miyata et al (2005) "Platelet-Derived Growth Factor-BB (PDGF-BB) Induces Differentiation of Bone Marrow Endothelial Progenitor Cell-Derived Cell Line TR-BME2 into Mural Cells, and Changes the Phenotype" J. Cell. Physiol. 204:948-955.
Morshed et al (2004) "Septic Arthritis of the Hip and Intrapelvic Abscess Following Intra-Articular Injection of Hylan G-F 20. A Case Report" J. Bone Joint Surg. Am. 86:823-826.
Munirah et al (2008) "Autologous Versus Pooled Human Serum for Articular Chondrocyte Growth" Journal of Orthopedic Surgery 16(2):220-229.
Muller et al (2006) "Animal Serum-Free Culture Conditions for Isolation and Expansion of Multipotent Mesenchymal Stromal Cells from Human BM" Cytotherapy 8(5):437-444.
Murphy et al (2003) "Stem Cell Therapy in a Caprine Model of Osteoarthritis" Arthritis Rheum. 48(12):3464-3474.
Murray et al (1999) "CD109 is Expressed on a Subpopulation of CD34$^+$ Cells Enriched in Hematopoietic Stem and Progenitor Cells" Exp. Hematol. 27:1282-1294.
Nakayama et al (2000) "Evaluation of Glycosaminoglycans Levels in Normal Joint Fluid of the Knee" J. Nippon Med. Sch. 67(2)92-95.
Nielsen et al (1990) "Postoperative Discitis. Radiology of Progress and Healing" Acta Radiol. 31(6):559-563.
Office Action Final dated Sep. 22, 2010 with respect to U.S. Appl. No. 11/773,774.
Office Action dated Nov. 6, 2009 with respect to U.S. Appl. No. 11/773,774.
Olweus et al (1995) "CD64/Fc Gamma RI is a Granulo-Monocytic Lineage Marker on CD34+ Hematopoietic Progenitor Cells" Blood 85(9):2402-2413.

(56) References Cited

OTHER PUBLICATIONS

Onofrio (1980) "Intervertebral Discitis: Incidence, Diagnosis, and Management" Clin. Neurosurg. 27:481-516.
Ordog et al (2004) "Purification of Interstitial Cells of Cajal by Fluorescence-Activated Cell Sorting" Am. J. Physiol. Cell Physiol 286(2):448-456.
Orpen and Birch (2003) "Delayed Presentation of Septic Arthritis of a Lumbar Facet Joint after Diagnostic Facet Joint Injection" J. Spinal Disord. Tech. 16(3):285-287.
Oshima et al (2004) "Fate of Transplanted Bone-Marrow-Derived Mesenchymal Cells During Osteochondral Repair using Transgenic Rats to Simulate Autologous Transplantation" OsteoArthritis Cartilage 12:811-817.
Otawa et al (2000) "Comparative Multi-Color Flow Cytometric Analysis of Cell Surface Antigens in Bone Marrow Hematopoietic Progenitors Between Refractory Anemia and Aplastic Anemia" Leukemia Research 24:359-366.
Park et al (2005) "Thoughts and Progress, Tissue-Engineered Cartilage Using Fibrin/Hyaluronan Composite Gel and its In Vivo Implantation" Artif. Organs 29(10):838-860.
Pellaton et al (1981) "Spectic Arthritis Following Repeated Intraarticular Injections of Glycosaminoglycanpolysulfat (Arteparon®) and Steroids for Osteoarthrosis of the Knee Joint" (French, English Abstract Only) Schweiz. Rudnsch. Med. Prax. 70(52):2364-2367.
Pietramaggiori et al (2006) "Freeze-Derived Platelet-Rich Plasma Shows Beneficial Healing Properties in Chronic Wounds" Wound Rep. Reg. 14:573-580.
Ponte and McDonald (1992) "Septic Discitis Resulting from *Escherichia coli* Urosepsis" J. Fam. Pract. 34(6):767-771.
Rasmusson et al (2003) "Mesenchymal Stem Cells Inhibit the Formation of Cytotoxic T Lymphocytes, but Not Activated Cytotoxic T Lymphocytes or Natural Killer Cells" Transplantation 76(8):1208-1213.
Reddi and Cunningham (1990) "Bone Induction by Osteogenin and Bone Morphogenetic Proteins" Biomaterials 11:33-34.
Richardson et al (2006) "Intervertebral Disc Cell-Mediated Mesenchymal Stem Cell Differentiation" Stem Cells 24:707-716.
Roberts et al (2003) "Autologous Chondrocyte Implantation for Cartilage Repair: Monitoring its Success by Magnetic Resonance Imaging and Histology" Arthritis Research and Therapy 5(1):R60-R73.
Rolf et al (1999) "Intra-Articular Absorption and Distribution of Ketoprofen After Topical Plaster Application and Oral Intake in 100 Patients Undergoing Knee Arthroscopy" Rheumatology 38:564-567.
Ruszymah (2004) "Autologous Human Fibrin as the Biomaterial for Tissue Engineering" Med. J. Malaysia 59 Suppl.B:30-1.
Sah et al "Effects of Fibrin Glue Components on Chondrocyte Growth and Matrix Formation," in 49th Annual Meeting of the Orthopaedic Research Society, poster #0721, 2003.
Sanchez et al (2003) "Is Platelet-Rich Plasma the Perfect Enhancement Factor? A Current Review" Int. J. Oral Maxillofac. Implants 18:93-103.
Sato et al (1999) "Reversible Expression of CD34 by Murine Hematopoietic Stem Cells" Blood 94(8):2548-2554.
Schallmoser et al (2007) "Human Platelet Lysate Can Replace Fetal Bovine Serum for Clinical-Scale Expansion of Functional Mesenchymal Stromal Cells" Transfusion 47(8):1436-1446.
Silverman et al (Jun. 1999) "Injectable Tissue-Engineered Cartilage Using a Fibrin Glue Polymer" Plast. Reconstr. Surg. 103(7):1809-1818.
Simmons and Torok-Storb (1991) "CD34 Expression by Stromal Precursors in Normal Human Adult Bone Marrow" Blood 78(11):2848-2853.
Singer et al (1987) "Simian Virus 40-Transformed Adherent Cells From Human Long-Term Marrow Cultures: Cloned Cell Lines Produce Cells with Stromal and Hematopoietic Characteristics" Blood 70(2):464-474.

Singer et al (1984) "Evidence for a Stem Cell Common to Hematopoiesis and its In Vitro Microenvironment: Studies of Patients with Clonal Hematopoietic Neoplasia" Leuk. Res. 8(4):535-545.
Spaggiari et al (2006) "Mesenchymal Stem Cell-Natural Killer Cell Interactions: Evidence that Activated NK Cells are Capable of Killing MSCs, Whereas MSCs can Inhibit IL-2-Induced NK-Cell Proliferation" Blood 107(4):1484-1490.
Stacey et al (2000) "Randomised Double-Blind Placebo Controlled Trial of Topical Autologous Platelet Lysate in Venous Ulcer Healing" Eur. J. Vasc. Endovasc. Surg. 20:296-301.
Terstappen et al (1991) "Sequential Generations of Hematopoietic Colonies Derived From Single Nonlineage-Committed CD34+CD38-Progenitor Cells" Blood 77(6): 1218-1227.
Toba et al (1999) "Novel Technique for the Direct Flow Cytofluorometric Analysis of Human Basophils in Unseparated Blood and Bone Marrow, and the Characterization of Phenotype and Peroxidase of Human Basophils" Cytometry 35(3):249-259.
Tondreau et al (2004) "Isolation of BM Mesenchymal Stem Cells by Plastic Adhesion or Negative Selection: Phenotype, Proliferation Kinetics and Differentiation Potential" Cyrotherapy 6(4):372-379.
Ueda et al (2007) "Induction of Senile Osteoporosis in Normal Mice by Intra-Bone Marrow-Bone Marrow Transplantation from Osteoporosis-Prone Mice" Stem Cells 25(6):1356-1363.
Weber (1988) "Infectious Damage to the Intervertebral Disk-Before and Following Discotomy" Z. Orthop Ihre Grenzeb 126(5):555-562 (German, English Abstract Only).
Willems et al (Jun. 2004) "Lumbar Discography: Should we Use Prophylactic Antibiotics? A Study of 435 Consecutive Discograms and a Systematic Review of the Literature" J. Spinal Disord. Tech. 17(3):243-247.
Willheim et al (1995) "Purification of Human Basophils and Mast Cells by Multistep Separation Technique and mAb to CDw17 and CD117/c-kit" J. Immunological Methods 182:115-129.
Xaymardan et al (2004) "Platelet-Derived Growth Factor-AB Promotes the Generation of Adult Bone Marrow-Derived Cardiac Myocytes" Circ Res. 94(5):E39-E45.
Yamada et al (2003) "Bone Regeneration Following Injection of Mesenchymal Stem Cells and Fibrin Glue with a Biodegradable Scaffold" J. Cranio-Maxillofac. Surg. 31:27-33.
Zhu et al (2006) "Hypoxia and Serum Deprivation-Induced Apoptosis in Mesenchymal Stem Cells" Stem Cells 24:416-425.
Centeno et al. (2008) The American Journal of Case Reports 9:201-206 "Increased Knee Cartilage Volume in Degenerative Joint Disease using Percutaneously Implanted, Autologous Mesenchymal Stem Cells, Platelet Lysate and Dexamethasone".
Centeno et al. (2008) Pain Physician 11(3):343-353 "Increased Knee Cartilage Volume in Degenerative Joint Disease using Percutaneously Implanted, Autologous Mesenchymal Stem Cells".
Centeno et al. (2011) Bioengineering & Biomedical Science S2:007 "A Case Series of Percutaneous Treatment of Non-Union Fractures with Autologous, Culture Expanded, Bone Marrow Derived, Mesenchymal Stem Cells and Platelet Lysate".
Ries et al. (2007) Blood 109(9):4055-4063 "MMP-2, MT1-MMP, and TIMP-2 are essential for the invasive capacity of human mesenchymal stem cells: differential regulation by inflammatory cytokines".
Xian and Foster (2006) Current Stem Cells Research and Therapy 1:213-229 "Repair of Injured Articular and Growth Plate Cartilage Using Mesenchymal Stem Cells and Chondrogenic Gene Therapy".
Gajdusek et al (1993) "Basic Fibroblast Growth Factor and Transforming Growth Factor Beta-1: Synergistic Mediators of Angiogenesis In Vitro" J. Cell. Physiol. 157(1):133-144.
Luis A. Solchaga et al (2002) "Treatment of Osteochondral Defects with Autologous Bone Marrow in a Hyaluronan-Based Delivery Vehicle", Tissue Engineering, vol. 8, No. 2, pp. 333-347.
Prins et al (1982) "Effect of Purified Growth Factors on Rabbit Articular Chondrocytes in Monolayer Culture. II. Sulfated Proteoglycan Synthesis" Arthritis & Rheumatism, 25(10):1228-1238.
Yang et al (1994) "Cardioprotective Effects of Platelets Against Ischaemia-Reperfusion Injury are Related in Part to Platelet Glutathione Redox Cycle" Cardiovasc. Res. 28(10): 1586-1593 ABSTRACT.

(56) References Cited

OTHER PUBLICATIONS

Ye et al (2007) "Effect of Three Growth Factors on Proliferation and Cell Phenotype of Human Fetal Meniscal Cells" Chinese Journal Reconstructive Surgery 21 (10):1137-1138 with English Abstract.

Zhu et al (2001) "Recombinant Human Acidic Fibroblast Growth Factor Accelerates the Healing of Full—Thickness Dermal Wounds in Pigs" Modern Rehabilitation 5(9):31 with English Abstract.

Leung et al., "Regeneration of intervertebral disc by mesenchymal stem cells: potentials, limitations, and future direction." Eur Spine Journal. 2006. vol. 15 (Suppl. 3), pp. S406-S413.

Grayson et al., "Hypoxia enhances proliferation and tissue formation of human mesenchymal stem cells", Biochemical and Biophysical Research Communications, 2007, vol. 358, pp. 948-953.

Rosova, et al. "Hypoxic Preconditioning Results in Increased Motility and Improved Therapeutic Potential of Human Mesenchymal Stem Cells." Stem Cells. 2008, vol. 26, pp. 2173-2182.

Grayson et al., "Effects of Hypoxia on Human Mesenchymal Stem Cell Expansion and Plasticity in 3D Constructions", Journal of Cellular Physiology, 2006, vol. 207, pp. 331-339.

Medical Dictionary definition of "undifferentiated", http://medical-dictionary.thefreedictionary.com/undifferentiated+cell, pp. 1-2, 2009-2012.

Wang et al., "Hypoxic preconditioning attenuates hypoxia-reoxygenation-induced apoptosis in mesenchymal stem cells", Acta Pharmacol. Sin., Jan. 2008, vol. 29, No. 1, pp. 74-82.

Hu et al., "Transplantation of hypoxia-preconditioned mesenchymal stem cells improves infarcted heart function via enhanced survival of implanted cells and angiogenesis", The Journal of Thoracic and Cardiovascular Surgery, 2008, vol. 135, No. 4, pp. 799-808.

Sotiropoulou et al. "Characterization of the Optimal Culture Conditions for Clinical Scale Production of Human Mesenchymal Stem Cells", Stem Cells. 2006, vol. 24. pp 462-471.

Hung et al., "Short-Term Exposure of Multipotent Stromal Cells to Low Oxygen Increases Their Expression of CX3CR1 and CXCR4 and Their Engraftment In Vivo", PLOS ONE, May 2007, 2(5), e416, pp. 1-11.

Biscoff et al., "Acidic pH stimulates the production of the Angiogenic CXC chemokine, CXCL8 (Interlukin-8), in human adult mesenchymal stem cells via the extracellular signal-regulated kinase and NF-kB pathways." Journal of Cellular Biochemistry. Feb. 2008, vol. 104, pp. 1378-1392.

Del Curling et al (1990) "Changing Concepts in Spinal Epidural Abscess: A Report of 29 Cases" Neurosurgery 27(2):185-192.

Neuhuber et al., "Effects of plating density and culture time on bone marrow stromal cell characteristics", Experimental Hematology. 2008, vol. 36, pp. 1176-1185.

\* cited by examiner

METHODS AND COMPOSITIONS TO FACILITATE REPAIR OF AVASCULAR TISSUE

CROSS-REFERENCE TO RELATED APPLICATIONS

The present application is a continuation application of co-pending U.S. patent application Ser. No. 13/132,840, which is a U.S. national stage application, filed under 35 U.S.C. § 371, of International Application No. PCT/US2009/066773, which was filed on Dec. 4, 2009, and which claims priority to U.S. Provisional Application No. 61/120,098, which was filed on Dec. 5, 2008 and U.S. Provisional Application 61/154,874, which was filed on Feb. 24, 2009. The contents of each are incorporated by reference into this specification.

TECHNICAL FIELD

The present invention provides compositions and methods for facilitating repair in a damaged avascular site, for example an intervertebral disc; more particularly, the invention provides applying environmentally conditioned autologous stem cells at optimized locations within avascular sites or adjacent to avascular sites in patients in need thereof.

BACKGROUND

Avascular transition zones and other hard to repair sites are present in a number of key tissues of the body. These zones are present where blood supply to the tissue, for example a disc, is limited or lacking or where damage to the tissue has caused a harsh environment that resists repair procedures. For example, when an avascular tissue is damaged, the lack or limit of blood supply to that tissue poses a significant hurdle to repair processes. This is particularly true in the intervertebral disc, knee and hip, where normal load issues make it difficult to facilitate repair and healing.

One particularly important avascular transition zone in the body is within the intervertebral disc, where there is no direct blood supply. Nutrients to the disc typically arrive via small capillary beds in the subchondral bone which diffuse throughout the disc over the course of time. In addition, discs receive nutrients via imbibitions, in other words by soaking up nutrients from surrounding tissue during axial loading activities such as walking, running and the like.

Intervertebral disc are shock absorbing pads that separate any two vertebrae of the spine from one another. These discs essentially provide three functions to a spine, first they act as shock absorbers to carry axial load of the body while in an upright position, second they act as a ligament to hold any two adjacent vertebrae together, and third they act as pivot points for enhanced bending and rotation of the spine.

Humans have 23 discs in their spine, i.e., 6 in the cervical region, 12 in the thoracic region, and 5 in the lumbar region. Each disc is composed of a nucleus pulposus, annulus fibrosus and vertebral end-plates. The nucleus pulposus is water-rich and gelatinous and comprises the center region of a disc. The annulus fibrosus is fibrous in nature, being made of collagen and includes little water (as compared to the nucleus pulposus) and surrounds the nucleus pulposus. A series of lamellae are arranged in the annulus fibrosus in order to contain the pressurized nucleus pulposus. In addition, vertebral end-plates act to attach each disc to adjacent vertebral bodies.

As discussed above, tissue repair and regeneration have proven difficult in damaged disc due to harsh environmental aspects of the disc (avascular, high pressure, adverse pH, etc) and the difficult mechanical requirements placed on a disc during repair (stress and strain associated with bipedal movement). Conventional repair methodologies that utilize stem cell technology have focused on direct implantation of stem cells (typically obtained from pre-existing non-autologous cell lines) into the nucleus pulposus, typically in the presence of a carrier material. While these methodologies have provided some hopeful results in animal models, these repairs have yet to be demonstrated in humans with degenerative disc disease (DDD) or other like conditions. The promising results in these animal models are likely due to the acute nature of the disc degeneration model used in animal research. For example, the discs in these animal models are newly degenerated with a better blood supply than a long standing degenerative disc in a human. In addition, the animals used in these models are generally quadrapedal versus humans who are bipedal and as such load discs differently. Finally, the animals used in these DDD models tend to be young and healthy, equivalent in age to patients who are much younger than the cohort commonly seen clinically with DDD. In general therefore, conventional methodologies are based on repair and regeneration in damaged disc environments potentially very different from those found in human patients in need of stem cell therapy.

Issues relevant to tissue repair and regeneration in the disc are also prevalent in the hip, knee, and shoulder (including rotator cuff). In each of these tissues, harsh environmental aspects are often established upon injury or aging, where avascular transition zones and difficult mechanical requirements combine to establish scenarios of low stem cell repair success.

The present invention is directed toward overcoming one or more of the problems discussed above.

SUMMARY OF THE EMBODIMENTS

The present invention provides compositions and methods for use in repair of damaged tissue having one or more poor nutritional zones or hostile environments, i.e., avascular zones. Poor nutritional zones or hostile environments are typically located where the tissue has limited or lacks vascular blood supply, i.e., termed avascular transition zones or avascular zones herein. Zones or environments in this light include: intervertebral disc, hip (labrum), shoulder (including rotator cuff) and other like sites. Embodiments herein include procurement of stem cells, for example mesenchymal stem cells, from a patient in need of repair in an avascular zone. Procured cells are then conditioned, in vitro, in an environment that allows for optimization of cells capacity to be used in repair of the patient's avascular zone. When a sufficient number of optimized, conditioned cells are present, cells are placed in target sites of the avascular zone in need of repair. In some embodiments, platelets or platelet lysate (typically autologous) and/or supplement treatments are placed in combination with the conditioned cells to enhance blood flow/nutrient flow to the site. Timing of the platelet and/or supplement treatment is typically just prior, during or just after placement of conditioned cells, although other timing regiments are contemplated. Procedures can be repeated to ensure repair of site, including repeat of only conditioned cell placement or platelet/platelet lysate/supplement treatment(s).

In one embodiment compositions and methods are provided for use in repair of damaged intervertebral discs in a patient in need thereof. In one aspect, methods are provided for procurement and culturing of stem cells under conditions which optimize the cells capacity to be used in repair and/or regeneration of a damaged disc. In another aspect, methods are provided for placement of these conditioned stem cells in targeted sites of the damaged disc to optimize growth and regeneration of the damaged disc tissue. In yet another aspect, methods are provided for placement of the conditioned stem cells in targeted sites within the patient in combination with treatment to the patient using epidural supplement treatment to enhance blood flow to and through the damaged disc. Additionally, the present invention provides improved compositions for stem cell culture dedicated toward selection of cells capable of repair and/or regeneration of a damaged disc. Individually, and/or in combination, the methods and compositions of the present invention provide surprising and unexpected advancements in the field of disc repair and regeneration (as compared to other conventional technologies).

In another embodiment, stem cells (mesenchymal stem cells, for example) are harvested from a patient in need of disc repair and cultured under conditions based on selecting and expanding cells able to withstand a poor nutritional environment, an otherwise hostile environment (for example one where pH is not in the ranges normally consistent with promoting healthy cell growth), a hypoxic environment, and/or an environment exhibiting elevated carbon dioxide levels within a damaged disc. These conditioned cells are then implanted in the fibrous posterior disc annulus (as compared to conventional methodologies which typically call for implantation in the nucleus pulposus). In some cases the patient is then treated with epidural supplements (growth factors, cytokines, integrins, cadherins, etc.) to facilitate blood flow to the posterior disc annulus. Each aspect of the embodiment increases and selects for stem cells capable of viability and expansion in the damaged disc environment as well as facilitates the disc environment to provide enhanced nutrition and oxygen to the implanted cells. In addition, autologous platelet or platelet lysate compositions can be administered separately or in combination with the selected stem cells to facilitate stem cell viability and expansion within the damaged disc. Individually or in combination the approaches herein enhance the repair process and results of autologous stem cell based disc repair.

In some instances, harvested stem cells from the patient in need of disc repair are cultured in vitro under 1-10% oxygen and more typically under 3 to 7% oxygen for a period of from 1 to 28 days. This can represent approximately $\frac{1}{3}$ to all of the time the cells are cultured prior to implantation within the patient. Surviving/viable cells, i.e., cells capable of growth under hypoxic conditions, are selected for viability and expanded under these hypoxic conditions to procure enough cells for implantation into the damaged disc. Selected cells have enhanced capability to survive, expand and ultimately repair within the oxygen deficient environment of a damaged disc.

In other instances, harvested stem cells from the patient in need of disc repair are cultured in vitro under elevated carbon dioxide and more typically under 2 to 10% carbon dioxide for a period of from 1 to 28 days. This can represent approximately $\frac{1}{3}$ to all of the time the cells are cultured prior to implantation within the patient. Surviving/viable cells, i.e., cells capable of growth under elevated carbon dioxide conditions, were selected for viability and expanded under these conditions to procure enough cells for implantation into the damaged disc. Selected cells have enhanced capability to survive, expand and repair within the higher carbon dioxide conditions of the environment of a damaged disc. This same approach can be used to select for stem cells used to repair/regenerate damaged (through injury or aging) hip and/or shoulder avascular sites.

In other instances, harvested stem cells from the patient in need of disc repair are cultured in vitro under both hypoxic and elevated carbon dioxide conditions. In vitro culture conditions can be maintained for a period of up to $\frac{1}{3}$ to all of the total culture time of the cells. Selected cells have enhanced capability to survive, expand and repair within the lower oxygen and higher carbon dioxide conditions typically found in damaged intervertebral disc. This same approach can be used to select for stem cells used to repair/regenerate damaged (through injury or aging) hip and/or shoulder avascular sites.

In still other instances, harvested stem cells from the patient in need of disc repair are cultured under nutrient poor conditions to select for viability and are expanded under these poor nutrient environments. Culture conditions include use of a basal cell culture media prepared from Dulbecco's Modified Essential Medium (DMEM) (or other like basal media) supplemented with sugars, amino acids, lipids, minerals, proteins, or other substances intended to facilitate stem cell growth. Growth media may or may not contain serum such as fetal calf serum, human whole serum, platelet rich plasma, platelet lysate, etc. . . . . However, these preparations are specifically designed to mimic the local environment of a human degenerated disc such as hypoxia, altered pH, or certain limited nutrient availability. This same approach can be used to select for stem cells used to repair/regenerate damaged (through injury or aging) hip (for example in labrum) and/or shoulder avascular sites.

Other selection conditions can be used to expand harvested stem cells including: pH, use of spent media, co-culture with nucleus pulposus cells, where the target site is in a damaged disc (thereby providing the environmental factors present from being in proximity to the ultimate target site for delivery of the cultured cells), and the like. Note also, in some instances two or more of the selection conditions described herein can be used to identify and expand stem cells for use in avascular site repair. So for instance, poor nutritional media and hypoxic conditions can be used to select for the stem cells used in a first patient, while pH and carbon dioxide conditions may be used for selection in a second patient. This may be based on actual measurements of the local micro environment in any given patient.

In still further instances, platelets, from the same patient having the damaged site, are procured (harvested) and treated with thrombin and calcium chloride ($CaCl_2$). Treated platelets are combined with cultured and selected stem cells for implantation into the damaged site. Note that treatment of the platelets can extend from one to seven days and more particularly from 5 to 7 days prior to implantation into damaged site. Additionally, platelets can be implanted just prior to, during or after implantation of the selected stem cells. Such preconditioned platelets are capable of releasing targeted growth factors into the avascular zone environment useful in facilitating stem cell survival and expansion within the damaged site. Alternatively, or in combination, growth factors, cytokines, integrins, etc can be directly administered with the selected stem cells into the damaged site. In one embodiment, these growth factors are administered around the exterior of, for example, a damaged disc such as placed into the epidural space.

These and various other features and advantages of the invention will be apparent from a reading of the following detailed description and a review of the appended claims.

DETAILED DESCRIPTION

Figure 1:
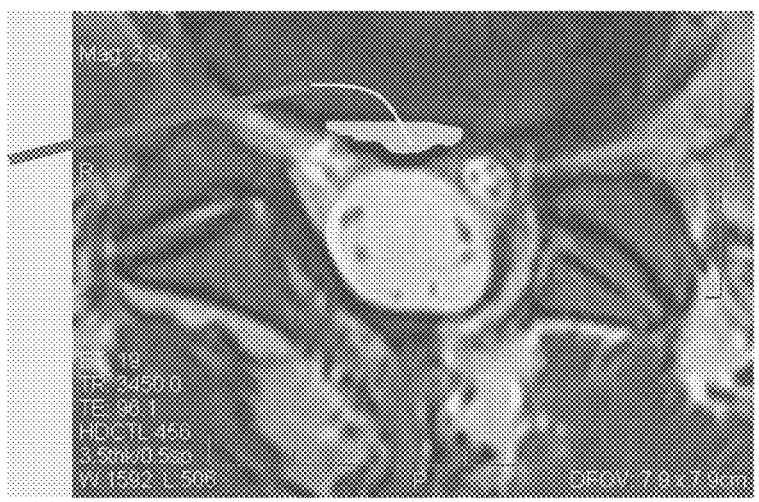
FIG. 1 is an axial lumbar view with superimposed path of needle placement of stem cells into the vascular and transitional vascular zones of the posterior disc annulus using embodiments described herein.

The present invention provides compositions and methods for use in repair of damaged tissue having one or more poor nutritional zones or hostile environments, i.e., avascular zones. Poor nutritional zones or hostile environments are typically located where the tissue has limited or lacks vascular blood supply, i.e., termed avascular transition zones herein. Zones or environments in this light include: intervertebral disc, hip, shoulder (including rotator cuff) and other like sites. Embodiments herein include procurement of stem cells, for example mesenchymal stem cells, from a patient in need of repair in an avascular zone. Procured cells are then conditioned, in vitro, in an environment that allows for optimization of cells capacity to be used in repair of the patient's avascular zone. When a sufficient number of optimized, conditioned cells are present, cells are placed in target sites of the avascular zone in need of repair. In some embodiments, supplement treatments are placed in combination with the conditioned cells to enhance blood flow/nutrient flow to the site. Timing of the supplement treatment is typically just prior, during or just after placement of conditioned cells, although other timing regiments are contemplated. Procedures can be repeated to ensure repair of site, including repeat of only conditioned cell placement or supplement treatment.

Avascular zone conditions for stem cell selection herein generally include: 1-10% oxygen, 2-10% carbon dioxide, altered pH, altered nutrition, and combinations of the like. Selected cells can be placed into repair sites in combination with supplements, e.g., growth factors, cytokines, integrins, cadherins, and the like, and/or with treated autologous platelets.

Definitions

The following definitions are provided to facilitate understanding of certain terms used frequently herein and are not meant to limit the scope of the present disclosure.

"Stem cell(s)" as used herein refers to cells possessing the properties of self-renewal and potency. With regard to mesenchymal stem cells, these cells are multipotent and have the capability to differentiate into osteoblasts, chondrocytes, myocytes, adipocytes, and other like cells.

Disc Bulge as used herein refers to a protrusion of the nucleus pulposis into the annulus fibrosis of the disc.

Disc Hernation as used herein refers to an extrusion of the nucleus pulposis beyond the confines of the annulus fibrosis.

Contained disc herniation as used herein refers to an extrusion of the nucleus pulposis beyond the confines of the annulus fibrosis and still confined by the posterior longitudinal ligament.

"Patient" as used herein refers to a mammal, and more typically a human, having one or more damaged or aged avascular sites, for example damaged intervertebral discs. With regard to a damaged disc, damage may include herniated disc, bulging disc, fractured disc, disc protrusion, disc extrusion, disc sequestration and other like disc ailments.

"Platelet and platelet lysate" are used interchangeably herein and include the combination of natural growth factors contained in platelets that have been released through lysing of the platelets. This can be accomplished through chemical means (i.e. $CaCl_2$), osmotic means (use of distilled $H_2O$), or through freezing/thawing procedures. Platelet lysates of the invention can also be derived from whole blood and can be prepared as described in U.S. Pat. No. 5,198,357, which is incorporated by reference herein.

"Repair" or "regeneration" are used interchangeably and refer to partial or complete replacement of a damaged area within a target avascular zone or a zone adjacent to the avascular zone. For example, repair of an intervertebral disc includes partial or complete repair or replacement of the tissue within the disc. Repair or regeneration can also refer to repair or regeneration of an avascular zone in a normally aging patient, i.e., repair damage to a zone induced by age.

"Environment" as used herein refers to the entire set of conditions that effect or influence cells in vitro or in vivo.

"Hypoxia or hypoxic" as used herein refers to an in vitro or in vivo condition having 10% or less oxygen in the environment.

"Supplement" or supplement treatments include growth factors, cytokines, integrins, including: VEGF-A, PlGF, VEGF-B, VEGF-C, VEGF-D, FGF, Ang1, Ang2, MCP-1 endoglin, TGF-β, CCL2, VE-cadherin, etc.

Embodiments in accordance with the present invention include methods and compositions useful in repair and regeneration of damaged avascular zones, e.g., intervertebral discs. Embodiments herein are predicated on the unexpected finding that harvest and expansion of autologous stem cells under poor nutritional and hypoxic conditions provide more capable cells for repair of an avascular zone. Further, implantation of conditioned cells with autologous platelets, as well as facilitating blood flow to the damaged site yield dramatically enhanced repair. Implantation can also include one or more supplement treatment(s) (with or without platelets). Finally, embodiments herein include administering these conditioned cells and ancillary materials at optimized sites within the damaged site to further facilitate repair and/or regeneration.

Stem Cells

Mesenchymal stem cells (MSCs) hold great promise as therapeutic agents in regenerative medicine. Alhadlaq, A. and J. J. Mao, Mesenchymal stem cells: isolation and therapeutics. Stem Cells Dev, 2004. 13(4): p. 436-48. Barry, F. P., Mesenchymal stem cell therapy in joint disease. Novartis Found Symp, 2003. 249: p. 86-96; discussion 96-102, 170-4, 239-41. Bruder, S. P., D. J. Fink, and A. I. Caplan, Mesenchymal stem cells in bone development, bone repair, and skeletal regeneration therapy. J Cell Biochem, 1994. 56(3): p. 283-94. Cha, J. and V. Falanga, Stem cells in cutaneous wound healing. Clin Dermatol, 2007. 25(1): p. 73-8. Gangji, V., M. Toungouz, and J. P. Hauzeur, Stem cell therapy for osteonecrosis of the femoral head. Expert Opin Biol Ther, 2005. 5(4): p. 437-42. These adult stem cells can be easily isolated from many sources in the body. Alhadlaq, A. and J. J. Mao, Mesenchymal stem cells: isolation and therapeutics. Stem Cells Dev, 2004. 13(4): p. 436-48. In addition, they have demonstrated in numerous animal studies, the ability to differentiate into muscle, bone, cartilage, nerves, tendon, and various internal organs cells. Lumbar disc degeneration and pathology are major causes of significant disability and medical expense. Dagenais, S., J. Caro, and S. Haldeman, A systematic review of low back pain cost of illness studies in the United States and internationally. Spine J, 2008. 8(1): p. 8-20. Surgical treatments such as discectomy, fusion, and disc replacement have been utilized in clinical practice, with strong potential for significant morbidity. de Kleuver, M., F. C. Oner, and W. C. Jacobs, Total disc replacement for chronic low back pain: background and a systematic review of the literature. Eur Spine J, 2003. 12(2): p. 108-16. Gotfryd, A. and O. Avanzi, A systematic review of randomized clinical trials using posterior discectomy to treat lumbar disc herniations. Int Orthop, 2008. Katonis, P., et al., Postoperative infections of the thoracic and lumbar spine: a review of 18 cases. Clin Orthop Relat Res, 2007. 454: p. 114-9. As a result, the ability to repair the Intervertebral disc (IVD) rather than surgical alteration or removal is an attractive treatment option. Saki and others have shown that MSC's are capable of lumbar disc repair in animal studies using a puncture model of simulated disc degeneration. Sakai, D., et al., Regenerative effects of transplanting mesenchymal stem cells embedded in atelocollagen to the degenerated intervertebral disc. Biomaterials, 2006. 27(3): p. 335-345. Sakai, D., et al., Differentiation of mesenchymal stem cells transplanted to a rabbit degenerative disc model: potential and limitations for stem cell therapy in disc regeneration. Spine, 2005. 30(21): p. 2379-87. Sakai, D., et al., Transplantation of mesenchymal stem cells embedded in Atelocollagen gel to the intervertebral disc: a potential therapeutic model for disc degeneration. Biomaterials, 2003. 24(20): p. 3531-41. The inventors recognized that there are many physiologic differences between animal and human IVD models. These include different forces created with quadrupeds in ovine, porcine and murine animals, versus bipedal mechanics in humans. In addition, the popular puncture model of degenerative disc disease (DDD), used by many animal researchers creates the scientific equivalent of an acutely injured disc. Human DDD is often present for decades prior to the patient seeking medical or surgical treatment. Embodiments herein (see Examples) show that MSC's percutaneously deployed into a posterior disc annulus of human subjects with VEGF enriched, platelet derived supernatant provides significant disc repair. The decision to place cells into the posterior disc annulus was based, partly, on the higher vascularization of this area versus the well defined avascular, low density nutrient environment within the nucleus pulposus.

Embodiments of the invention include harvest of stem cells from the patient in need of avascular site repair. Stem cells in accordance with the invention are as described above in the definitions section. In some embodiments the stem cells are mesenchymal stem cells, i.e., multipotent cells capable of differentiating into, among other cell types, osteoblasts, chondrocytes, myocytes, adipocytes and pancreatic islet cells. Note that for purposes of the invention many embodiments are described in relation to mesenchymal stem cells, although other stem cell types can also be used and are within the scope of the present invention.

Stem cell harvest in accordance with aspects of the present invention include those described in US Patent Application S/N PCT/us08/68202 which are incorporated by reference in there entirety. Additionally, methods and compositions as described in U.S. Pat. Nos. 5,486,359, 6,387, 367 and 5,197,985 are incorporated by reference herein in their entirety.

In more detail, mesenchymal stem cells are multipotent stem cells located in the bone marrow, peripheral blood, adipose tissue and other like sources. MSCs have the capacity to differentiate into a number of cell types, including osteoblasts, chondrocytes, myocytes, adipocytes, and beta-pancreatic islet cells.

Source MSCs of the invention are typically harvested from the iliac crest of the patient in need (or other source such as the IVD, periosteum, synovial fluid, or the vertebral body or pedicle) of the restorative/replacement therapy (or a suitable donor), such patient is referred to herein as a "patient in need or patient in need thereof" (note that other sources, such as adipose tissue, synovial tissue, and connective tissue have recently been identified and are also considered as MSC sources within the scope of the present invention. In one embodiment, approximately 10-100 cc of bone marrow is harvested and "isolated" using methods described in U.S. Patent Application 60/761,441 to Centeno or through adherence to plastic, as described in U.S. Pat. No. 5,486,359 to Caplan et al. Each of these references is incorporated herein in their entirety for all purposes.

As described in more detail below embodiments of the present invention may also require some level or amounts of platelets. As such, this invention incorporates changes to standard marrow draw procedures to allow appropriate nucleated cell number yield to use platelets or platelet lysate techniques. In addition, these platelets can be obtained from whole blood. Since the vast majority of the published research is again performed in healthy humans or animals, the application of this technique to humans with various disease states has never been tested. Note that, the use of an altered technique drawing three small 2-3 cc marrow aliquots on each side (total of 6 aliquots), produced the required nucleated cell yield which was successfully expanded in 20% platelet lysate.

Platelets and platelet lysate for use herein is prepared from the bone marrow harvest using the method of Doucet (Doucet, Ernou et al., 2005 J. Cell Physiol 205(2): 288-36), which is incorporated by reference herein in its entirety. Typical lysates include from about tens of millions to 100's of billions platelets. As shown by Martineau et al., Biomaterials, 2004 25(18) p 4489-503 (incorporated herein by reference in its entirety), platelet lysates inherently include the growth factors required to facilitate consistent MSC growth. In typical embodiments the platelet lysate and MSC are autologous and are in amounts useful for effective and consistent expansion of the MSCs (described more fully below). In particular, it should be noted that while the levels of growth factors such as TGF-beta are much lower in platelet lysate than those commonly used to expand MSC's, it is believed that there are significant synergistic effects when all of the low level growth factors contained in platelet lysate are used together.

Stem Cell Selection (Selective Pressure)

Harvested stem cells are cultured to select for stem cells (typically mesenchymal stem cells) and ultimately for stem cells that are viable and expand under environmental conditions similar to those conditions found in a site in need of repair, for example a disc in need of repair. Selective pressure as it relates to intervertebral disc repair is discussed in greater detail below, but similar conditions are present and ascertainable for conditions required for hip, shoulder and the like.

As discussed in Urban et al., Nutrition of the intervertebral Disc. Spine, 2004. 29 (23): p 2700-9, (incorporated herein by reference in its entirety), intervertebral disc that have suffered injury and are degenerative provide a poor nutritional as well as oxygen environment. This environment is distinct from the environment of a healthy intervertebral disc. In fact, studies performed to determine viability of transplanted mesenchymal stem cells in injured disc show poor cell viability results, with few cells capable of expanding to provide the necessary numbers of cells needed for enhanced disc repair (Wuertz et al., Behavior of mesenchymal stem cells in the chemical microenvironment of the intervertebral disc. Spine, 2008. 33(17): p 1843-9, incorporated herein by reference in its entirety).

In more detail, harvested stem cells from a patient in need of disc repair or restoration are placed under culture conditions. In one embodiment, the culture medium is a basal cell culture medium prepared from DMEM or other like media. Culture medium can be supplemented with sugars, amino acids, lipids, minerals, proteins, or other like substances intended to facilitate stem cell expansion.

In addition, embodiments herein can include culturing harvested and expanding mesenchymal stem cells under various atmospheric conditions that simulate a damaged disc's environment. In one embodiment, harvested stem cells are cultured in vitro under 1-15% oxygen. In some cases the harvested stem cells are cultured under 3 to 10% oxygen and in other cases the harvested stem cells are cultured under 3 to 7% oxygen. These lower oxygen conditions replicate the hypoxic conditions present in typical damaged disc environments. Hypoxic conditions can be present for part or all of the stem cell expansion period but is typically present for at least ⅓ of the time that cells are cultured in vitro. Selection occurs as cells are cultured, with viable cells that are able to survive and ultimately expand having an advantage when implanted into a disc having a hypoxic environment.

In other embodiments, harvested stem cells are cultured in vitro under elevated carbon dioxide conditions, typically from 2-10% carbon dioxide. Harvested cells can additionally be cultured in a combined elevated carbon dioxide and hypoxic environment, where conditions include from 2-10% carbon dioxide and from 3-10% oxygen. As above, selection occurs as cells are cultured, with viable cells that are able to survive and ultimately expand having an advantage when implanted into a disc having an elevated carbon dioxide environment or an elevated carbon dioxide environment combined with a hypoxic environment.

In other embodiments, harvested stem cells are cultured and expanded in combination with harvested and cultured nucleas pulposis cells (NP cells) or annulus fibrosis cells (AF cells). The nucleas pulposis (NP) cells for co-culture with stem cells can be harvested from the patient in need of disc repair via a needle aspirate or other like technique. These NP cells or AF cells can be either autologous or non-autologous. In typical embodiments, approximately $10^3$ to $10^9$ NP or AF cells are co-cultured with the harvested stem cells and are allowed to provide an environment useful for selection of stem cells that respond to NP cell and/or AF cell released factors and waste products. Co-culture conditions can include poor nutritional environment, hypoxia, elevated carbon dioxide and other disclosed embodiments described herein. In some embodiments, the NP cells are cultured in a separate in vitro flask (or other like container) from the stem cells. The spent media from the NP cell culture can then be combined with media conditions above during stem cell culture or can be used exclusively to expand and select for stem cells able to maintain viability and ultimately expand under such conditions.

In other embodiments, harvested stem cells are cultured and expanded under modified pH conditions similar to those found in a damaged intervertebral disc. For example, in vitro culture media (as described herein) can be modified to have a pH of from 6.6-7.0, and more typically from 6.7 to 6.9. Modified pH can be combined with any of the culture conditions discussed herein to facilitate selection of stem cells for use in disc repair and regeneration.

In other embodiments, harvested stem cells are cultured and expanded under modified osmolarity conditions similar to those found in a damaged intervertebral disc. For example, in vitro culture media (as described herein) can be modified to have an osmolarity of from 350-600 mOsm, and more typically from 450 to 500 MOsm. Modified osmolarity can be combined with any of the culture conditions discussed herein to facilitate selection of stem cells for use in disc repair and regeneration.

In other embodiments, viability and expansion of stem cells under one or more selection conditions can be modified by inclusion of one or more growth factors. In these cases, cells under selection are cultured in the presence of TGF-beta FGF, PDGF, IGF and/or HIF-1 alpha, including mixtures thereof and other like factors.

Note that for each of the above stem cell culture based embodiments, the condition(s) can be gradually incorporated into cells standard culture environment. For example, harvested stem cells may be initially cultured under 10% oxygen for one or two passages, then moved to 9% oxygen conditions for one or two passages, and cultured under decreasing levels of oxygen until a target hypoxic condition is obtained. Under this procedure, cells are gradually allowed to adapt to an environment present in a damaged disc.

The following treatment procedure is described in relation to treatment of a damaged disc, although treatment of other avascular zones are envisioned to be within the scope of the present invention.

Treatment of Damaged Intervertebral Disc

Stem cells having been selected for by at least one of the above discussed damaged disc modifiers are allowed to expand until a sufficient number of cells are present for implantation into a patient's damaged disc. In typical embodiments, from about $10^5$ to $10^9$ selected mesenchymal stem cells are required for implantation into the damaged disc.

Cultured cells are washed using PBS or other like buffer to obtain a cell population that does not include materials not intended for implantation into the patient's body, i.e., media constituents, waste products, etc. Washed stem cells can include NP cells, although it is contemplated that where stem cells are co-cultured with NP cells, that the NP cell population can be removed via cell sorting techniques or affinity chromatography. Stem cells are now ready for implantation into the patient in need thereof.

In one embodiment, the washed stem cells are implanted directly into the posterior annulus of the damaged disc. This is an unexpected location for implantation of stem cells, as conventional methodologies show implantation of cells into the nucleas pulposis. Cells are implanted into the posterior annulus of the damaged disc via known techniques in the art, including via percutaneous x-ray guided or surgical IVD access. One or more iteration of cell implantation can be used in repair procedure for a damaged disc, although, a period of 14 to 180 days is typical between treatments.

In another embodiment, autologous platelets from the patient in need of therapy are pretreated with thrombin and $CaCl_2$ for approximately one to seven days. This treatment preconditions these platelets to preferentially express vascular endothelial growth factor (VEGF). In some embodiments, the harvested platelets are pretreated with approximately 28.56 U/ml thrombin and approximately 2.86 mg/ml $CaCl_2$. In additional embodiments, autologous platelets from the patient in need thereof are pretreated with a combination of thrombin, calcium or its' salts, thromboxane A2, adenosine triphosphate, and arichidonate. As above, pretreatment can be from one to seven days prior to implantation into the patient in need thereof. The preconditioned autologous platelets are then implanted before, during or after implantation of the previously discussed selected conditioned stem cells of the invention. Platelets are generally implanted in the same location as the implanted stem cells.

In another embodiment, harvested and selected stem cells of the invention are implanted with one or more supplement or supplement treatments, including growth factors, cytokines, integrins, cadherins, or molecules or drugs known to promote angiogenesis, vasculogenesis or aerteriogenesis, including: VEGF-A, PlGF, VEGF-B, VEGF-C, VEGF-D, TGF-β, Ang-1, Ang-2, IGF, HGF, FGF, Tie2, PDGF, CCL2, Alpha-V Beta-5, Alpha-5 Beta-1, VE-cadherin, PECAM-1, plasminogen activator and nitrogen oxide synthase. In alternative embodiments, stem cells for use in implantation in patients in need thereof are co-implanted with a combination of growth factors including TGF-β, FGF, PDGF, IGF or other like growth factors intended to promote stem cell and/or mesenchymal stem cell stemness or proliferation. In some embodiments autologous platelets or platelet lysates can be implanted in combination with the before mentioned supplements.

FIG. 1 illustrates the utility of one embodiment of the invention showing an axial lumbar view with a superimposed needle placement. Conditioned stem cells using embodiments described herein were placed in the vascular and transition vascular zones of the posterior disc annulus.

EXAMPLES

Example 1

Percutaneously Implanted Autologous Mesenchymal Stem Cells

Methods:
Subjects:
Three patient subjects were selected based on willingness to participate in an IRB (Spinal Injury Foundation, Westminster, Colo.) approved MSC implantation protocol. Each subject signed an IRB approved consent form. Subjects were selected based on the following inclusion/exclusion criterion:

Inclusion Criteria:
1. 18-65 years of age
2. Failure of conservative management
3. Lumbar degenerative disc disease with a disc protrusion or contained disc extrusion (subligamentous)
4. Selective nerve root blocks that confirmed the disc protrusion/nerve to be treated as the pain generator (>75% relief of major pain complaint) or discography which confirmed the disc as a P2 pain generator
5. At least 75% of normal disc height with or without dehydration on T2 weighted MRI images
6. Unwillingness to pursue surgical options Exclusion Criteria:
1. Active inflammatory or connective tissue disease (i.e. lupus, fibromyalgia, RA)
2. Active non-corrected endocrine disorder potentially associated with symptoms (i.e. hypothyroidism, diabetes)
3. Active neurologic disorder potentially associated with symptoms (i.e. peripheral neuropathy, multiple sclerosis)
4. Severe cardiac disease
5. Pulmonary disease requiring medication usage
6. A history of dyspnea or other reactions to transfusion of autologous blood products Pre-Procedure Data Collection:
1. CBC and blood chemistries were obtained within 3 months of the MSC implantation to rule out unknown medical conditions.

2. Pre-procedure MRI
3. Pre-procedure outcomes measures

Isolation and Expansion of Mesenchymal Stem Cells (MSCs):

For one week prior to the marrow harvest procedure the patient was restricted from taking corticosteroids or NSAIDs. Coincident with the marrow harvest procedure, heparinized (Abraxis Pharmaceuticals) IV venous blood was drawn to be used for platelet lysate (PL). Platelet lysate was prepared via centrifugation at 200 g to separate platelet rich plasma (PRP) from red blood cells (RBCs). PRP volume was aliquoted and stored at −20° C. to produce PL. Platelet lysate was supplemented in cell culture media at 10-20%.

A platelet derived VEGF rich supernatant was also prepared based on the method described by Martineau. (Martineau, I., E. Lacoste, and G. Gagnon, *Effects of calcium and thrombin on growth factor release from platelet concentrates: kinetics and regulation of endothelial cell proliferation.* Biomaterials, 2004. 25(18): p. 4489-502). Using the same PRP isolation steps as above, the PRP was drawn off and an aliquot was activated with 28.56 U/mL of human thrombin (Johnson and Johnson) and 2.85 mg/mL of Calcium Chloride ($CaCl_2$, American Regent) for 6 days at 37° C. and 5% $CO_2$. Activated PRP samples were centrifuged at 3,000 rpm for 6 minutes, supernatant was draw off and stored at −80° C. This was later used as both injectate to be mixed with culture expanded MSC's as well as for supplement injections to be delivered via epidural injection.

Coincident with the whole IV blood draw, the patient was then placed prone on an operating room (OR) table and the area to be harvested was anesthetized with 1% Lidocaine, and a sterile disposable trocar was used to draw 10 cc of marrow blood from the right PSIS area and 10 cc from the left PSIS area, in heparinized syringes. If the patient reported pain during the marrow draw that was not easily controlled by local anesthetics, a caudal epidural with anesthetic only was added.

Figure 2:
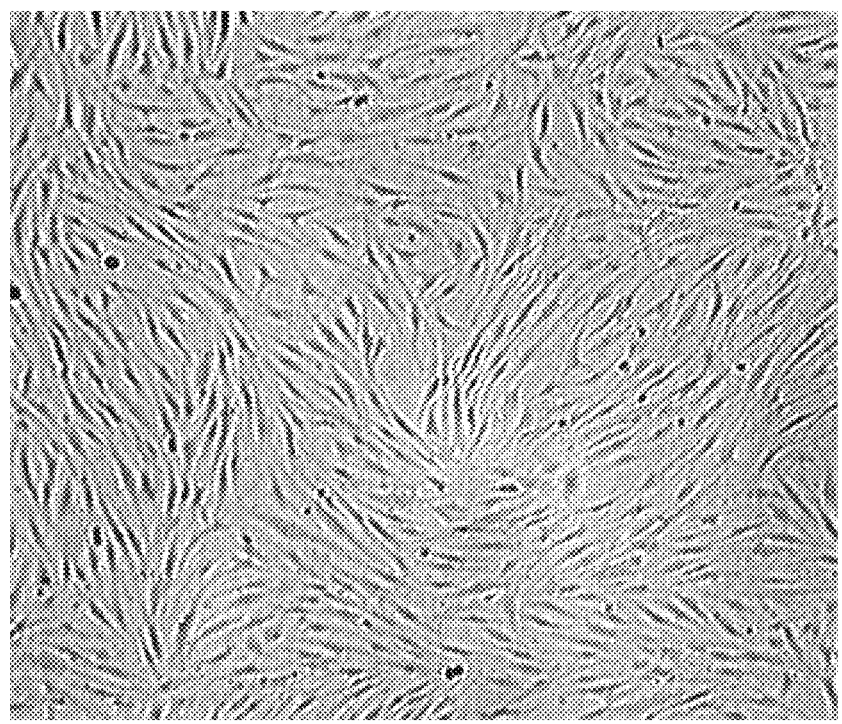
FIG. 2 shows MSCs grown in monolayer culture according to a technique provided herein.

Whole marrow was centrifuged at 200 g for 4-6 minutes to separate the nucleated cells from the RBCs. The nucleated cells were removed and placed in a separate tube. Samples were centrifuged at 1000 g for 6 minutes to pellet. The nucleated cells were washed once in phosphate buffered saline (PBS, GibCo), counted, and then re-suspended in Dulbecco's modified eagle medium (DMEM, GibCo) with 10-20% PL, 5 ug/mL doxycyline (Bedford Labs), and 2 IU/mL heparin (Abraxis Pharmaceuticals). Nucleated cells were seeded at $1\times10^6$ cells/cm$^2$ in a tissue culture flask. Cultures were incubated at 37° C./5% $CO_2$/5% $O_2$ in a humidified environment. The culture medium was changed after 48-72 hours, removing the majority of the non-adherent cell population. The MSC colonies developed in 6-12 days and then were harvested with animal origin-free trypsin like enzyme (TrypLE Select, GibCo) such that only the colony-forming MSCs detached. To expand the MSCs, they were plated at a density between 6-12,000 cells/cm$^2$ in alpha-modified eagle medium (AMEM, GibCo) with 10-20% PL, 5 ug/mL doxycyline, and 2 IU/mL of heparin, and grown to near confluence at 37° C./5% $CO_2$/5% $O_2$. Primary cells derived from the bone marrow were designated as passage 0 and each subsequent subculture of MSCs was considered one further passage. See FIG. 2 for an example of the MSC morphology grown with this monolayer cell culture technique. After MSC's had been sub cultured to the 2nd-5th passage, they were harvested, washed, and suspended in the activated PRP for injection.

Percutaneous Implantation Procedure

Figure 3:
FIG. 3 is an exemplary fluoroscopy image of the injection location of MSCs and platelet derived VEGF supernatant into the posterior disc annulus of the L5-S1 disc (subject ML). Note the concentration of contrast in the posterior disc annulus (contrast flow enhanced with blue).

Subjects were positioned prone on an x-ray table and prepped using betadine swab with sterile gloves and drapes. An AP fluoroscopy view (Siemens Iso-C) was obtained with an ipsilateral oblique orientation. The superior endplate of the targeted level to be injected was visualized "on end" by adjusting cephalic-caudal tilt. Using sterile technique, a 22 gauge 7 inch quinke needle was guided under bi-planar fluoroscopy to the superior articular process of the lumbar facet joint of the level to be treated and advanced past the facet into the posterior disc. Once the disc access was obtained, under lateral view, the needle was positioned to maximize contrast flow (Omnipaque 300 mg/ml-NDC 0407-1413-51 diluted 50% with PBS) into the posterior annulus as close to the anatomic position of the disc protrusion as possible, using pretreatment MRI imaging for approximation (see FIG. 3). Culture expanded autologous MSC's in platelet derived VEGF supernatant were then injected and the needle was extracted.

Figure 4:
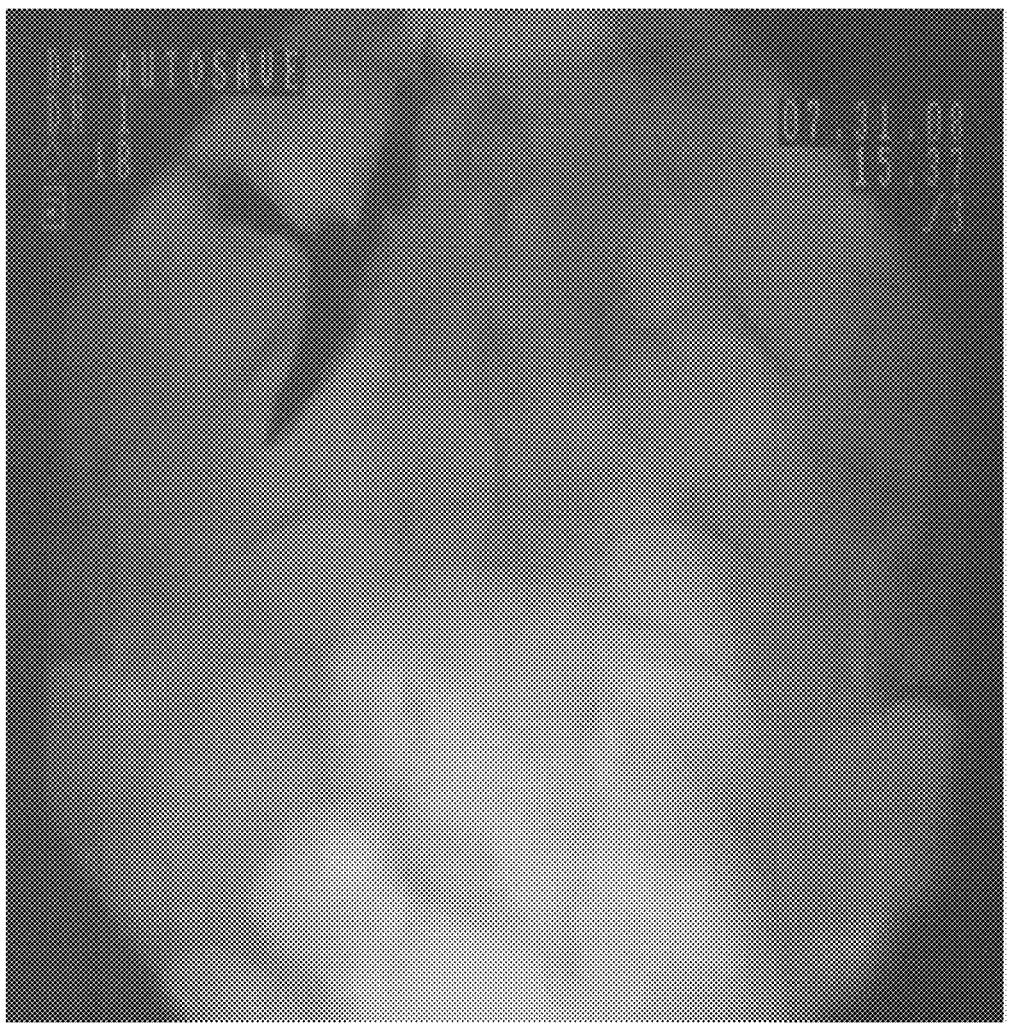
FIG. 4 demonstrates exemplary epidural flow attained with the platelet derived VEGF supernatant injections that were performed after the stem cell transplant.

Following MSC implantation, at week 1 and week 2 the subject returned for additional transformainal epidurals performed with VEGF derived supernatant at the target levels. Epidural procedures were performed with the same preparation. Epidural access was obtained using a 25 gauge 3.5 inch quince needle which was manipulated under biplanar fluoroscopy and directed toward the subpedicular recess of the target level being injected. Once good epidural dye flow extending upwards and under the pedicle was visualized, the VEGF derived supernatant plus 4% lidocaine was injected and the needle was extracted (see FIG. 4). Post-op treatment protocol consisted of lumbar traction in physical therapy or at home at 3 times a week for four weeks.

Imaging and Patient Follow-Up:

A GE 3.0 Tesla Excite HD was used to image the lumbar spine. Imaging sequences included a sagittal Short Tau Inversion Recovery (STIR), Fast Gradient Recall Echo (FGRE) sagittal, and a Gradient Recall Echo Fast Spin (GRE-FS). Images were viewed and measured in E-Film Workstation Version 1.5.3 (Merge Healthcare). Sagittal short tau inversion recovery (STIR) and gradient recall echo (GRE) fast spin images with matching TR/TE and matching imaging planes were used. This was performed to reduce the likelihood of interpretation error of serial images in the same patient. To reduce diurnal effects, the imaging center was instructed to perform the serial films as close to the same time of day as possible.

Follow-up questionnaires were initiated via phone and obtained from the patient concerning function and symptoms. Modified VAS scores were obtained with regard to low back pain and a "Functional Rating Index" (FRI) was also obtained. This questionnaire focuses on patient function. (Feise, R. J. and J. Michael Menke, Functional rating index: a new valid and reliable instrument to measure the magnitude of clinical change in spinal conditions. Spine, 2001. 26(1): p. 78-86; discussion 87). Office visits were also used for post-op examinations. These were initiated at the following intervals:

1. At 6 weeks post procedure.
2. At 12 weeks post procedure

Results:

Medical histories and outcomes of the three subjects enrolled are described below:

Patient 1:

HO was a 19 year old white female, college athlete with a 7 year history of low back pain thought to be secondary to lifting trauma and her chosen sport. She had undergone extensive conservative care for four years prior to presentation, including evaluation and treatment with an interventional pain management physician The lumbar facets were ruled out as pain generators with negative response to intra-articular injections, MRI showed an L5-S1 disc protrusion abutting both S1 nerve roots, worse on the right side. Discography revealed a symptomatic posterior annular tear with concordant reproduction of pain at the L5-S1 disc. Pre-procedure the subject described constant pain of variable severity, with numbness and tingling in the S1 distribution of the right foot with any physical activity, resulting in significant functional limitations.

Figure 11:
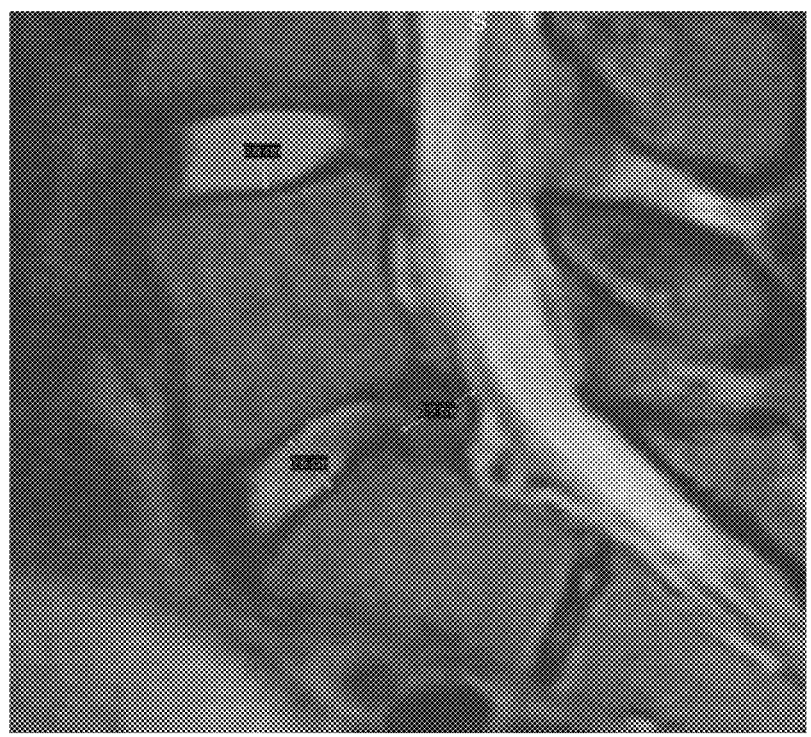
FIG. 11 provides HO pre-procedure sagittal STIR slice through the maximum extent of the L5-S1 disc protrusion. ET=6, TR=4816.7, TE=48.3. Image time of day was 11:26 a.m. The L5-S1 disc protrusion is measured at 9 mm. Disc heights measure: L4-L5=6 mm, L5-S1=8 mm.
Figure 12:
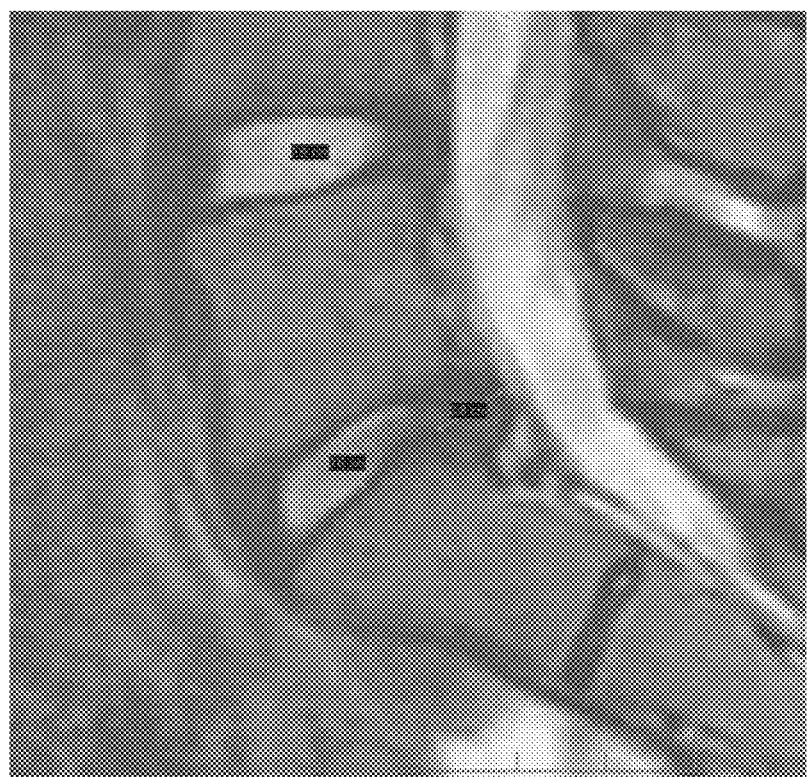
FIG. 12 provides HO 6 week post procedure sagittal matching STIR slice. Imaging parameters kept constant at ET=6, TR=4816.7, TE=48.3. Image time of day was 11:25 a.m. The L5-S1 disc protrusion is measured at 8 mm. Disc heights measure: L4-L5=6 mm, L5-S1=8 mm.
Figure 13:
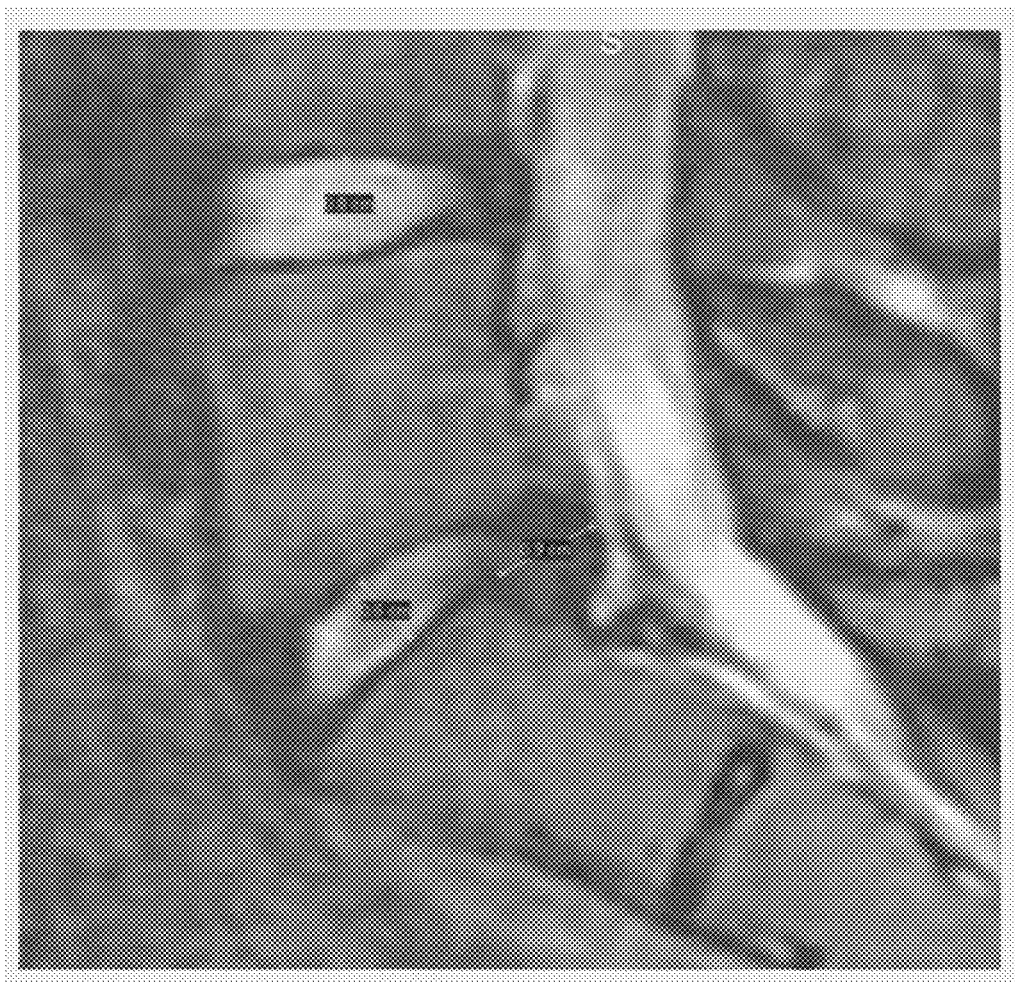
FIG. 13 provides HO 3.5 month post procedure matching sagittal STIR slice. Imaging parameters kept constant at ET=6, TR=4816.7, TE=48.3. Image time of day was 1:10 p.m. The L5-S1 disc protrusion is measured at 9 mm. Disc heights measure: L4-L5=6 mm, L5-S1=8 mm.

The subject reported up to 75% improvement through 12 weeks. At 6 months post procedures, the subject showed little change in her reported modified VAS pain scores and Functional Rating Index. There was a corresponding lack of change seen in the post-treatment MRI imaging results. A 1 mm reduction in maximum protrusion size was seen at 6 weeks, but this returned to pre-procedure size at 3.5 months. All disc height measurements remained the same across all imaging sessions and the maximum time of day interval for all images taken was 1 hour and 45 minutes. Results for the HO are shown in FIGS. 11, 12 and 13.

Patient 2:

MJM was a 35 year old white male with a 15 year history of low back pain prior to presentation. He reported failed conservative care and increasing frequency of severe pain episodes due to activity. MRI revealed a lumbarized S1-S2 segment, a broad-based disc bulge with moderate facet encroachment and moderate foraminal narrowing at L5-S1. Additionally, there was a right greater than left posterior contained protrusion at L4-L5. The physical examination revealed no active radiculopathy, but the patient reported intermittent radicular symptoms associated with exacerbations. Surgery was recommended after failure on conservative management, but was declined. The L4-L5 disc was the focus of this treatment with the dehydrated L5-S1 disc left as a control.

Figure 8:
FIG. 8 provides MJM pre-procedure sagittal slice through the maximum extent of the contained L4-L5 disc extrusion. Image was taken at 12:15 pm. ET=6, TR=4816.7, TE=48.1. The L4-L5 disc extrusion is measured at 6 mm. Disc heights measured at the mid-portion of the disc on this slice were: L4-L5=8 mm, L5-S1=7 mm, S1-S2=5 mm.
Figure 9:
FIG. 9 provides MJM 2 months post-procedure matching sagittal STIR slice with same imaging parameters. ET=6, TR=4816.7, TE=48.1. Image was taken at 12:35 pm. The L4-L5 disc extrusion is measured at 3 mm. Disc heights measured the same as pre-procedure: L4-L5=8 mm, L5-S1=7 mm, S1-S2=5 mm.
Figure 10:
FIG. 10 provides MJM 4.5 months post-procedure. This is matching sagittal STIR slice with same imaging parameters. ET=6, TR=4833.3, TE=48.2. Image was taken at 12:27 pm. The L4-L5 disc extrusion is measured at 3 mm. Disc heights measured the same as pre-procedure: L4-L5=8 mm, L5-S1=7 mm, S1-S2=5 mm.

Six months post procedure, the patient improvement of modified VAS from 3 to a 0 with a drop in frequency of pain by more than 80% (see Table 1). The FRI score for this patient increased by more than 60% and he reported overall symptom improvement at 50%. L4-L5 disc bulge sagittal STIR image measured 6 mm at its maximum extent in the pre-op MR images (see FIG. 8). In both the 2 month and 4.5 month follow-up films (matching image sequence and slice- see FIGS. 9 and 10) the L4-L5 bulge was found to be reduced to 3 mm with no change in disc heights measured at any of the L4-S2 discs. The time of day when the images were acquired varied by no more than 20 minutes.

Figure 5:
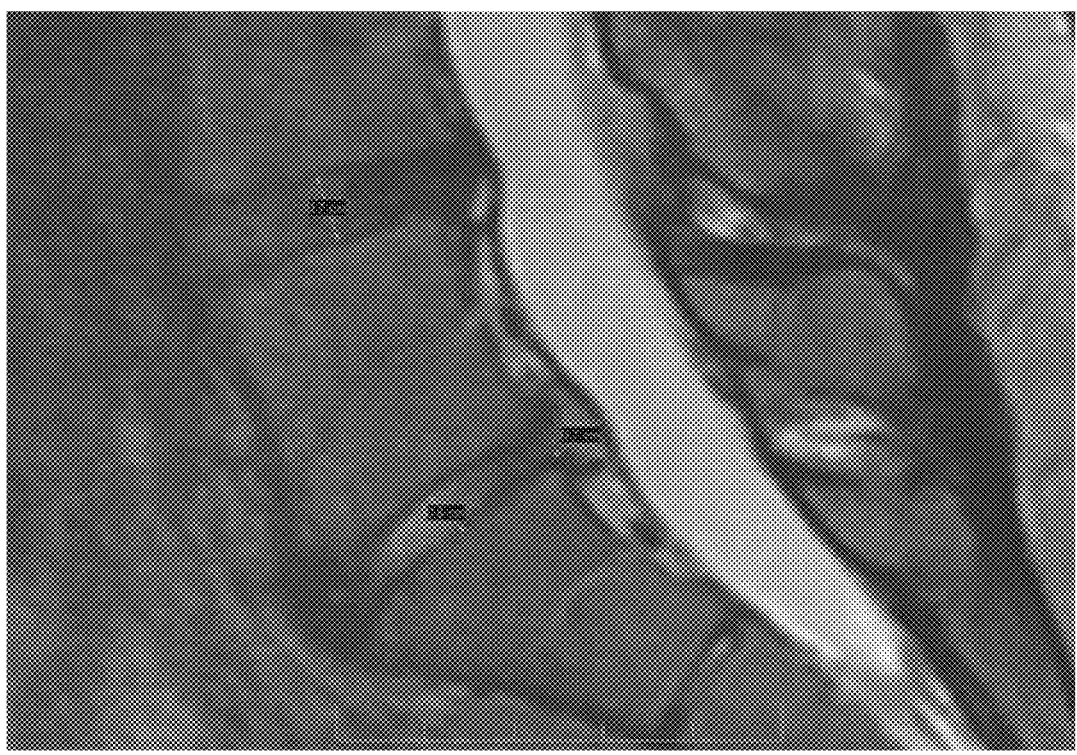
FIG. 5 provides ML Short Tau Inversion Recovery (STIR) image taken less than 1 month prior to procedure. This sagittal slice is chosen as it represents the maximum extent of the contained L5-S1 disc extrusion. ET=6, TR=4816.7, TE=48.1 with an imaging time of day of 1:01 p.m. This image demonstrates a 0.7 cm disc extrusion at L5-S1. L5-S1 disc height measured at central disc is 0.5 cm with L4-L5 measuring at 0.7 cm.

Patient 3:

ML was a 24 year old white female with a traumatic low back injury associated with a military training exercise. At the time of presentation she had been symptomatic for three years. Her complaints consisted of electric shooting pain down one and sometimes both legs, low back pain with prolonged sitting or standing, and pain with bending or stooping. She had failed conservative management consisting of physical therapy. The pre-procedure MM demonstrated decreased disc height but somewhat preserved T2 signal in the L5-S1 disc (see FIG. 5). This disc also had an extrusion of 0.7 cm that was contained by the posterior longitudinal ligament. The posterior annulus was disrupted and there was a high intensity zone from the nucleus pulposus to the posterior longitudinal ligament. The L4-L5 disc had less T2 signal and was dehydrated, but had preservation of disc height. There was a protrusion at this level measuring 0.4 cm with a high intensity zone seen in the inferomedial portion of the disc. Based on the history, examination and MRI findings, intermittent traversing nerve root irritation at L5 and S1 roots was suspected at both L4-L5 and L5-S1 disc levels. Discogram was performed showing low pressure concordant pain (P2) at both L4-L5 and L5-S1, both with posterior annular tears. The decision was made to treat only the L5-S1 disc with the MSC injection, leaving L4-L5 to serve as an untreated control.

Figure 6:
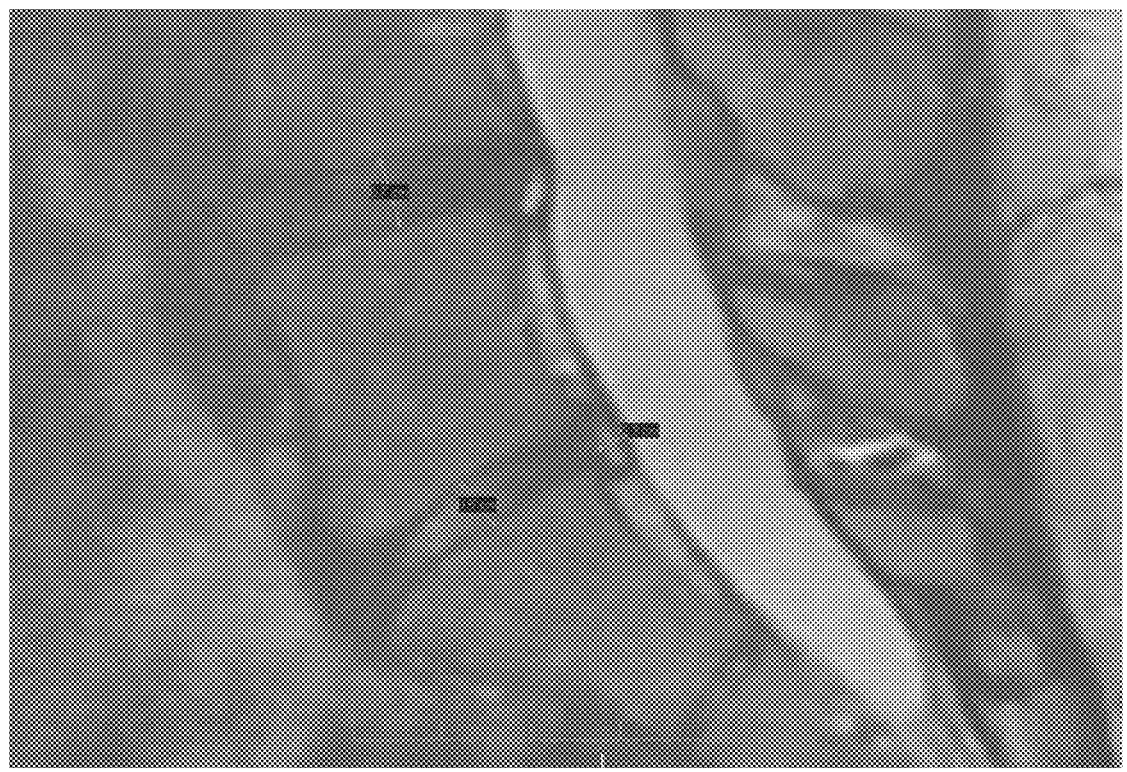
FIG. 6 provides ML 1 month post procedure matching sagittal slice using the same STIR parameters. ET=6, TR=4816.7, TE=48.1. Imaging time of day was 11:01 a.m. This image demonstrates a 0.3 cm disc extrusion at L5-S1. Note disc heights 0.5 cm at L5-S1 and 0.7 cm at L4-L5.
Figure 7:
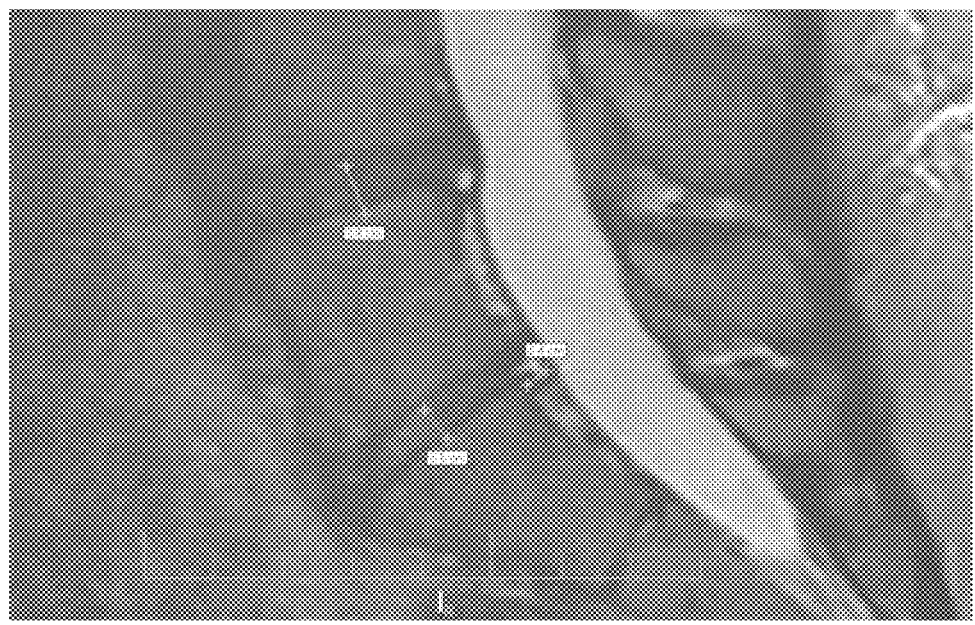
FIG. 7 provides ML 5 month post procedure matching sagittal slice using the same STIR parameters. ET=6, TR=4816.7, TE=48.3. Imaging time of day was 10:23 a.m. This image demonstrates a 0.3 cm disc extrusion at L5-S1. Note disc heights 0.5 cm at L5-S1 and 0.7 cm at L4-L5.

At 6 months post procedure (see Table 1) ML reported improvement of approximately 40% in low back modified VAS (1-10 scale) with a decrease of greater than 60% in frequency of pain. Function improved as measured by FRI by more than 70%. She self reported symptom improvement of 60%. Her post-procedure lumbar MRI imaging demonstrated that the size of the L5-S1 disc protrusion decreased from 0.7 cm pre-procedure to 0.3 cm at 1 month post procedure and 0.4 cm at 5 months post procedure (see FIGS. 6 and 7). Additionally, the size of the HIZ area in the posterior disc annulus decreased in both follow-up films. The time of image acquisition differed by a no more than 1.5 hours.

TABLE 1

Pre-procedure and 6 month post procedure reported outcomes for low back modified VAS and frequency. Frequency of 1.0 equals constant pain. Functional Rating Index measurements as well as self report of percentage change in condition.

| Subject | VAS-pre AVG | VAS-post AVG | VAS-pre AVG frequency | VAS-post AVG frequency | FRI-pre | FRI-post | Self-Reported Outcome |
|---|---|---|---|---|---|---|---|
| ML | 4 | 2 | 1.00 | 0.38 | 44 | 13 | 60% improvement |
| MJM | 3 | 1 | 1.00 | 0.13 | 23 | 9 | 50% improvement |
| HO | 7 | 4 | 1.0 | 1.0 | 27 | 25 | No lasting improvement |

TABLE 2

Total MSC yields and time in culture.

| Subject | Final MSC Yield in Millions | Days in Culture |
|---|---|---|
| ML | 14.3 | 18 |
| MJM | 33.0 | 17 |
| HO | 28.5 | 17 |

Figure 14:
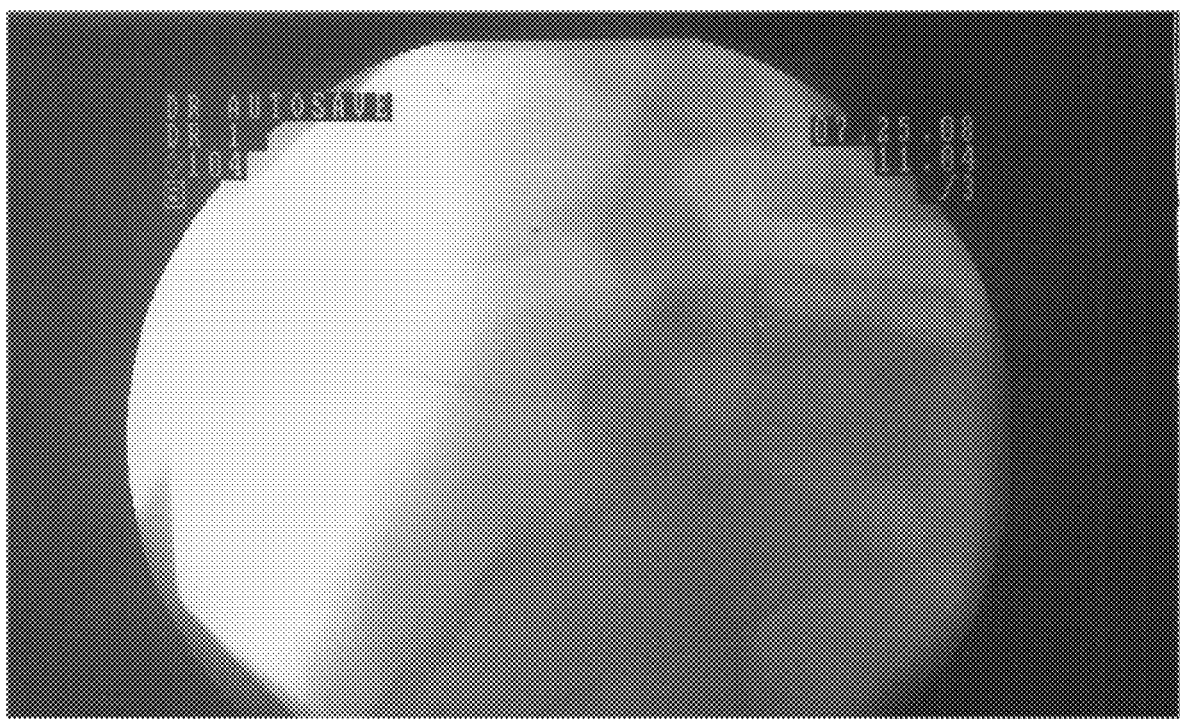
FIG. 14 shows contrast flow in HO (enhanced in blue) was more typical of a nucleogram than the intended target which was the posterior disc annulus.

Discussion:

Two of the three treated subjects demonstrated a decrease in the size of the treated disc protrusion and reported sustained subjective and functional improvement. A single subject demonstrated a temporary decrease in symptoms and a small transient change in the size of the disc protrusion, followed by regression to pretreatment baseline measures. Of interest, placing cells preferentially into the posterior disc annulus of this patient was technically difficult, with suboptimal flow of contrast into the posterior annulus. The inventors question possible correlation between this suboptimal placement and the subject's lack of sustained response. Koga et al. has demonstrated that MSC's injected nonspecifically into the intra-articular space failed to repair cartilage lesions, but those applied directly on the defect, allowing attachment at the target tissue were capable of repair. Note that HO's contrast flow and subsequent MSC flow (see FIG. 14) was primarily into the nucleus pulposus. Our own unpublished clinical experience in placing mesenchymal stem cells directly into the nucleus pulposus of other patients failed to initiate any observable MRI changes. These observations would also support the concept that location of stem cell adherence may be critical to the success of treatment. In particular, the posterior disc annulus maintains some vascular perfusion, while the avascular nucleus pulposus has a well documented suboptimal nutritional environment, which may result in a lack of sustainability of implanted MSC's. Martin, M. D., C. M. Boxell, and D. G. Malone, Pathophysiology of lumbar disc degeneration: a review of the literature. Neurosurg Focus, 2002. 13(2): p. E1. Also of note, HO had the least prolific stem cell yield, producing significantly fewer cells over a longer culture period than the other subjects. (see Table 2).

Since MSC's have a fibroblastic morphology in monolayer culture (see FIG. 2) the observed results could have been due to fibroblastic differentiation of the MSC's placed preferentially into the posterior disc annulus. Awad, H. A., et al., In vitro characterization of mesenchymal stem cell-seeded collagen scaffolds for tendon repair: effects of initial seeding density on contraction kinetics. J Biomed Mater Res, 2000. 51(2): p. 233-40. Delorme, B. and P. Charbord, Culture and characterization of human bone marrow. Mesenchymal stem cells. Methods Mol Med, 2007. 140: p. 67-81. Xiang, Y., et al., Ex vivo expansion and pluripotential differentiation of cryopreserved human bone marrow mesenchymal stem cells. J Zhejiang Univ Sci B, 2007. 8(2): p. 136-46.

Alternatively, the other variable which may have contributed to a therapeutic effect was the follow up platelet supernatant epidural injections. Martineau et al. has shown that a platelet supernatant prepared using specific calcium and thrombin preconditioning, produces a maximal burst of VEGF degranulation from platelets (as well as a host of other growth factors). Martineau, I., E. Lacoste, and G. Gagnon, Effects of calcium and thrombin on growth factor release from platelet concentrates: kinetics and regulation of endothelial cell proliferation. Biomaterials, 2004. 25(18): p. 4489-502. VEGF is known to cause angiogenesis and the human degenerative intervertebral disc (IVD) is known to suffer from poor vascular perfusion. Maroudas, A., et al., Factors involved in the nutrition of the human lumbar intervertebral disc: cellularity and diffusion of glucose in vitro. J Anat, 1975. 120(Pt 1): p. 113-30. Wallace, A. L., et al., Humoral regulation of blood flow in the vertebral endplate. Spine, 1994. 19(12): p. 1324-8. Pandya, N. M., N. S. Dhalla, and D. D. Santani, Angiogenesis—a new target for future therapy. Vascul Pharmacol, 2006. 44(5): p. 265-74.

An alternative explanation for the decrease in IVD protrusion in these patients may have been attributed to diurnal effects. Park et al. demonstrated changes in the size of disc bulges in 8 asymptomatic volunteers at L4-L5 when Mills were performed in the morning and evening. Park, C. O., Diurnal variation in lumbar MRI. Correlation between signal intensity, disc height, and disc bulge. Yonsei Med J, 1997. 38(1): p. 8-18. While this effect could have occurred in these subjects, two of the patients had untreated control discs that did not change in size. In addition, the single imaging center responsible for the MRI studies was instructed to perform follow-up scans as close as possible to the same time of day as the initial scans. As a result, the maximum time of day variance between images for any patient was less than 2 hours. Finally, treated and control disc heights were measured and no significant changes were noted for all subjects. If diurnal changes had been present, one would expect significant variation in disc height due to the effects of imbibition. An alternative explanation for reduction in disc protrusion size could be a healing effect induced directly by needle trauma. Korecki et al. investigated this effect in an in-vitro animal model and found the opposite to be true, needle puncture likely caused biomechanical injury to the disc and a reduction in its overall function. Korecki, C. L., J. J. Costi, and J. C. Iatridis, Needle puncture injury affects intervertebral disc mechanics and biology in an organ culture model. Spine, 2008. 33(3): p. 235-41. Additionally, it should be noted that the standard model for inducing DDD in animals is via puncture injury. Niinimaki, J., et al., Quantitative magnetic resonance imaging of experimentally injured porcine intervertebral disc. Acta Radiol, 2007. 48(6): p. 643-9.

CONCLUSIONS

This Example demonstrates that percutaneously implanted autologous MSC's with platelet supernatant epidural supplementation is capable of reducing the size of contained lumbar disc protrusion. Although it is unclear why one of the patients did not respond to the therapy, it is reasonable to hypothesize that lack of response was attributable to comparatively low MSC yield, as well as the sub-optimal placement of the MSCs.

The data in this Example shows the utility of one embodiment of the invention where procedures described herein provide a surprising improvement in repair over other procedures described in the art. Data with regard to other avascular repair sites, e.g., shoulder, hip, etc, is expected to show similar levels of improvement.

Various embodiments of the disclosure could also include permutations of the various elements recited in the claims as if each dependent claim was multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

This specification contains numerous citations to patent, patent application, and publications. Each is hereby incorporated by reference for all purposes.

What is claimed is:

1. A method for treating an avascular zone in a patient in need thereof, the method comprising:
    an isolation and expansion process consisting of:
        obtaining whole marrow from the patient in need thereof;
        centrifuging the whole marrow to separate nucleated cells from red blood cells;

removing the nucleated cells from the centrifuged whole marrow;

washing and counting the nucleated cells;

culturing the nucleated cells in a culture medium under a selective pressure of about 1% to about 10% oxygen for 1-28 days, wherein the culture medium is maintained at a pH from 6.6 to 6.9 and the culture medium comprises 10% to 20% human platelet lysate;

selecting viable mesenchymal stem cells capable of growth in the culture medium under the selective pressure of about 1% to about 10% oxygen;

an implantation process comprising:

providing the selected, viable, mesenchymal stem cells for implantation in the avascular zone;

implanting platelet cell lysate or platelets prior to, during, or after implanting the selected, viable, mesenchymal stem cells;

wherein the implanting of the platelet cell lysate or platelets and the selected, viable, mesenchymal stem cells is in the avascular zone.

2. The method of claim 1, wherein the culture medium has an osmolarity of about 350 mOsm to about 600 mOsm.

3. The method of claim 1, wherein about $10^5$-$10^9$ selected, viable mesenchymal stem cells are implanted.

4. The method of claim 1, wherein the implanting also includes, either separately or in combination, epidural supplements, growth factors, cytokines, integrins, and cadherins to facilitate blood flow.

5. The method of claim 1, wherein the selected, viable mesenchymal stem cells are implanted into a degenerative intervertebral disc.

6. The method of claim 5, wherein the selected, viable mesenchymal stem cells are implanted into a posterior disc annulus of the degenerative intervertebral disc.

7. A method for treating an avascular zone in a patient in need thereof, the method comprising:

an isolation and expansion process consisting of:

obtaining whole marrow from the patient in need thereof;

centrifuging the whole marrow to separate nucleated cells from red blood cells;

removing the nucleated cells from the centrifuged whole marrow;

washing and counting the nucleated cells;

culturing the nucleated cells in a culture medium under a selective pressure of about 10% oxygen and then culturing the nucleated cells under decreasing levels of oxygen until about 1% oxygen, wherein the culturing from about 10% oxygen to about 1% oxygen is for 1-28 days wherein the culture medium is maintained at a pH from 6.6 to 6.9 and the culture medium comprises 10% to 20% human platelet lysate;

selecting viable mesenchymal stem cells capable of growth in the culture medium under the selective pressure of about 10% to about 1% oxygen;

an implantation process comprising:

providing the selected, viable mesenchymal stem cells for implantation in the avascular zone;

implanting platelet cell lysate or platelets prior to, during, or after implanting the selected, viable mesenchymal stem cells;

wherein the implanting of the platelet cell lysate or platelets and the selected, viable mesenchymal stem cells is in the avascular zone.

8. The method of claim 7, wherein the culture medium has an osmolarity of about 350 mOsm to about 600 mOsm.

9. The method of claim 7, wherein about $10^5$-$10^9$ selected, viable mesenchymal stem cells are implanted.

10. The method of claim 7, wherein the implanting also includes, either separately or in combination, epidural supplements, growth factors, cytokines, integrins, and cadherins to facilitate blood flow.

11. The method of claim 7, wherein the selected, viable mesenchymal stem cells are implanted into a degenerative intervertebral disc.

12. The method of claim 11, wherein the selected, viable mesenchymal stem cells are implanted into a posterior disc annulus of the degenerative intervertebral disc.

13. A method for treating an avascular zone in a patient in need thereof, the method comprising:

an isolation and expansion process consisting of:

obtaining whole marrow from the patient in need thereof;

centrifuging the whole marrow to separate nucleated cells from red blood cells;

removing the nucleated cells from the centrifuged whole marrow;

washing and counting the nucleated cells;

culturing the nucleated cells in a culture medium under a selective pressure of about 10% oxygen and then culturing the nucleated cells under decreasing levels of oxygen until about 5% oxygen, wherein the culturing from about 10% oxygen to about 5% oxygen is for 1-28 days, wherein the culture medium is maintained at a pH from 6.6 to 6.9 and the culture medium comprises 10% to 20% human platelet lysate;

selecting viable mesenchymal stem cells capable of growth in the culture medium under the selective pressure of about 10% to about 5% oxygen;

an implantation process comprising:

providing the selected, viable mesenchymal stem cells for implantation in the avascular zone;

implanting platelet cell lysate or platelets prior to, during, or after implanting the selected, viable mesenchymal stem cells;

wherein the implanting of the platelet cell lysate or platelets and the selected, viable mesenchymal stem cells is in the avascular zone.

\* \* \* \* \*